(12) United States Patent
Baroni et al.

(10) Patent No.: US 9,682,050 B2
(45) Date of Patent: Jun. 20, 2017

(54) METHODS OF TREATING LACTOSE INTOLERANCE

(71) Applicant: Nogra Pharma Limited, Dublin (IE)

(72) Inventors: Sergio Baroni, Villa D'adda (IT); Salvatore Bellinvia, Balerna (CH); Francesca Viti, Salorino (CH)

(73) Assignee: Nogra Pharma Limited, Dublin (IE)

( * ) Notice: Subject to any disclaimer, the term of this patent is extended or adjusted under 35 U.S.C. 154(b) by 0 days.

(21) Appl. No.: 14/394,916

(22) PCT Filed: Apr. 12, 2013

(86) PCT No.: PCT/EP2013/057729
§ 371 (c)(1),
(2) Date: Oct. 16, 2014

(87) PCT Pub. No.: WO2013/156413
PCT Pub. Date: Oct. 24, 2013

(65) Prior Publication Data
US 2015/0087678 A1    Mar. 26, 2015

Related U.S. Application Data

(60) Provisional application No. 61/672,931, filed on Jul. 18, 2012.

(30) Foreign Application Priority Data

Apr. 18, 2012 (EP) .................................... 12425073

(51) Int. Cl.
| | | |
|---|---|---|
| A61K 31/196 | (2006.01) | |
| A61K 31/195 | (2006.01) | |
| A61K 31/4439 | (2006.01) | |
| A61K 31/606 | (2006.01) | |
| A61K 31/635 | (2006.01) | |
| A23C 9/152 | (2006.01) | |
| A23C 9/20 | (2006.01) | |
| A23C 13/12 | (2006.01) | |
| A23C 21/08 | (2006.01) | |
| A23C 19/09 | (2006.01) | |

(52) U.S. Cl.
CPC ............ *A61K 31/196* (2013.01); *A23C 9/152* (2013.01); *A23C 9/20* (2013.01); *A23C 13/12* (2013.01); *A23C 19/09* (2013.01); *A23C 21/08* (2013.01); *A61K 31/195* (2013.01); *A61K 31/4439* (2013.01); *A61K 31/606* (2013.01); *A61K 31/635* (2013.01)

(58) Field of Classification Search
CPC .. A61K 31/196; A61K 31/195; A61K 31/606; A61K 31/635; A61K 31/4439; A23C 19/09; A23C 9/20; A23C 13/12; A23C 21/08; A23C 9/152
See application file for complete search history.

(56) References Cited

U.S. PATENT DOCUMENTS

| | | |
|---|---|---|
| 3,211,610 A | 10/1965 | Rogers |
| 3,444,232 A | 5/1969 | Bernstein |
| 4,036,951 A | 7/1977 | Halpern et al. |
| 4,348,223 A | 9/1982 | Grove |
| 4,404,215 A | 9/1983 | Vincent et al. |
| 4,429,152 A | 1/1984 | Gries et al. |
| 4,720,506 A | 1/1988 | Munakata et al. |
| 4,869,913 A | 9/1989 | Gries et al. |
| 4,933,330 A | 6/1990 | Jorgensen et al. |
| 5,262,549 A | 11/1993 | Telfer et al. |
| 5,302,751 A | 4/1994 | Manimaran et al. |
| 5,519,014 A | 5/1996 | Borody |
| 5,594,015 A | 1/1997 | Kurtz et al. |
| 5,594,151 A | 1/1997 | Stolowitz |
| 6,114,382 A | 9/2000 | Moretti |
| 6,194,627 B1 | 2/2001 | Geissler et al. |
| 6,326,364 B1 | 12/2001 | Lin et al. |
| 6,403,656 B1 | 6/2002 | Rivier et al. |
| 6,583,128 B2 | 6/2003 | Ekwuribe et al. |
| 6,602,869 B1 | 8/2003 | Galey et al. |
| 6,844,003 B2 | 1/2005 | Galey et al. |
| 6,884,821 B1 | 4/2005 | Shinoda et al. |
| 6,903,082 B2 | 6/2005 | Ekwuribe et al. |
| 7,098,025 B1 | 8/2006 | Auwerx et al. |
| 7,176,204 B2 | 2/2007 | Miyachi et al. |
| 7,425,578 B2 | 9/2008 | Ekwuribe et al. |
| 7,429,676 B2 | 9/2008 | Woltering et al. |
| 7,749,980 B2 | 7/2010 | Plourde, Jr. et al. |
| 7,998,474 B2 | 8/2011 | Kelly |
| 8,030,520 B2 | 10/2011 | Sundermeier et al. |
| 8,138,357 B2 | 3/2012 | Naccari et al. |
| 8,153,693 B2 | 4/2012 | Baroni et al. |
| 8,153,841 B2 | 4/2012 | Naccari et al. |

(Continued)

FOREIGN PATENT DOCUMENTS

| | | |
|---|---|---|
| EP | 0055689 A1 | 7/1982 |
| EP | 0102833 A1 | 3/1984 |

(Continued)

OTHER PUBLICATIONS

Medow et al (Am. J. Dis. Child, Nov. 1990, 144(11):1261-4).*
Tzameli et al (The Journal of Biological Chemistry, 2004, vol. 279, No. 34, Issue of Aug. 20, pp. 36093-36102).*
Ahnfelt-Ronne et al. (1990) "Clinical Evidence Supporting the Radical Scavenger Mechanism of 5-Aminosalicylic Acid," Gastroenterology, 98:1162-1169.
Allgayer, H. (2003) "Review Article: Mechanisms of Action of Mesalazine in Preventing Colorectal Carcinoma in Inflammatory Bowel Disease," Aliment Pharmacol. Ther., 18 (Suppl. 2): 10-14.

(Continued)

*Primary Examiner* — Sudhakar Katakam
(74) *Attorney, Agent, or Firm* — Goodwin Procter LLP

(57) ABSTRACT

Disclosed herein are methods for treating lactose intolerance, including compounds that may be specific or modulate PPARγ receptors.

9 Claims, 5 Drawing Sheets

(56) References Cited

U.S. PATENT DOCUMENTS

| | | | |
|---|---|---|---|
| 8,450,506 B2 | 5/2013 | Naccari et al. | |
| 8,501,806 B2 | 8/2013 | Baroni et al. | |
| 8,710,100 B2 | 4/2014 | Naccari et al. | |
| 8,754,127 B2 | 6/2014 | Baroni et al. | |
| 8,796,334 B2 | 8/2014 | Baroni et al. | |
| 9,133,099 B2 | 9/2015 | Naccari et al. | |
| 9,345,680 B2 | 5/2016 | Naccari et al. | |
| 9,511,041 B2 | 12/2016 | Baroni et al. | |
| 2003/0113815 A1 | 6/2003 | Houseknecht et al. | |
| 2003/0133875 A1 | 7/2003 | Kelly | |
| 2003/0220374 A1 | 11/2003 | Needleman | |
| 2003/0229083 A1 | 12/2003 | Debnath et al. | |
| 2004/0034067 A1 | 2/2004 | MacPhee | |
| 2004/0115127 A1 | 6/2004 | Wright et al. | |
| 2004/0132110 A1 | 7/2004 | Desreumaux et al. | |
| 2006/0159648 A1 | 7/2006 | Davis et al. | |
| 2006/0177444 A1 | 8/2006 | Horizoe | |
| 2006/0270635 A1 | 11/2006 | Wallace et al. | |
| 2007/0086967 A1 | 4/2007 | MacDonald | |
| 2007/0149804 A1 | 6/2007 | Woltering et al. | |
| 2009/0048343 A1 | 2/2009 | Naccari et al. | |
| 2009/0118357 A1 | 5/2009 | Naccari et al. | |
| 2010/0305077 A1 | 12/2010 | Baroni et al. | |
| 2011/0105748 A1 | 5/2011 | Bhuniya et al. | |
| 2011/0152225 A1* | 6/2011 | Baroni | A61K 31/136 514/166 |
| 2011/0288058 A1 | 11/2011 | Baroni et al. | |
| 2011/0288177 A1 | 11/2011 | Baroni et al. | |
| 2012/0053244 A1 | 3/2012 | Baroni et al. | |
| 2012/0053245 A1 | 3/2012 | Baroni et al. | |
| 2012/0157417 A1 | 6/2012 | Baroni et al. | |
| 2012/0316230 A1 | 12/2012 | Naccari et al. | |
| 2013/0005813 A1 | 1/2013 | Naccari et al. | |
| 2015/0045436 A1 | 2/2015 | Naccari et al. | |
| 2015/0051285 A1 | 2/2015 | Baroni et al. | |
| 2015/0087708 A1 | 3/2015 | Baroni et al. | |
| 2015/0148418 A1 | 5/2015 | Baroni et al. | |
| 2015/0250749 A1 | 9/2015 | Giuliani et al. | |
| 2015/0265514 A1 | 9/2015 | Giuliani et al. | |
| 2015/0265562 A1 | 9/2015 | Naccari et al. | |
| 2015/0265563 A1 | 9/2015 | Naccari et al. | |
| 2016/0338927 A1 | 11/2016 | Baroni et al. | |

FOREIGN PATENT DOCUMENTS

| | | | |
|---|---|---|---|
| EP | 0279096 A2 | 8/1988 | |
| EP | 0291159 A2 | 11/1988 | |
| EP | 0352826 A2 | 1/1990 | |
| EP | 0623104 B1 | 8/1997 | |
| EP | 0938459 B1 | 7/2002 | |
| EP | 1285908 A1 | 2/2003 | |
| EP | 1348698 A1 | 10/2003 | |
| EP | 0554291 B1 | 12/2003 | |
| EP | 1373906 A1 | 1/2004 | |
| EP | 1389044 A1 | 2/2004 | |
| EP | 1607103 A1 | 12/2005 | |
| EP | 1274407 B1 | 3/2006 | |
| EP | 1801093 B1 | 3/2009 | |
| EP | 1448995 B1 | 1/2011 | |
| EP | 2298321 A1 | 3/2011 | |
| EP | 2107047 B1 | 9/2011 | |
| GB | 767788 A | 2/1957 | |
| GB | 1359560 | 7/1974 | |
| IT | WO 2008104557 A1 * | 9/2008 | A61K 31/136 |
| JP | 2003-516310 A | 5/2003 | |
| JP | 3425441 B2 | 7/2003 | |
| JP | 3435651 B2 | 8/2003 | |
| JP | 2004-528329 A | 9/2004 | |
| JP | 2005-510733 A | 4/2005 | |
| JP | 2009-242399 A | 10/2009 | |
| WO | WO-92/06690 A1 | 4/1992 | |
| WO | WO-93/14056 A1 | 7/1993 | |
| WO | WO-94/00135 A1 | 1/1994 | |
| WO | WO-95/31194 A1 | 11/1995 | |
| WO | WO-96/30016 A2 | 10/1996 | |
| WO | WO-97/25042 A1 | 7/1997 | |
| WO | WO-98/06387 A2 | 2/1998 | |
| WO | WO-98/43081 A1 | 10/1998 | |
| WO | WO-99/15520 A1 | 4/1999 | |
| WO | WO-00/59866 A1 | 10/2000 | |
| WO | WO-00/62766 A2 | 10/2000 | |
| WO | WO-01/02388 A1 | 1/2001 | |
| WO | WO-01/25181 A1 | 4/2001 | |
| WO | WO-01/79153 A1 | 10/2001 | |
| WO | WO-02/46161 A1 | 6/2002 | |
| WO | WO-02/095393 A2 | 11/2002 | |
| WO | WO-03/033481 | 4/2003 | |
| WO | WO-03/046580 A1 | 6/2003 | |
| WO | WO-2004/073622 A2 | 9/2004 | |
| WO | WO-2005/012280 A1 | 2/2005 | |
| WO | WO-2005/040102 A2 | 5/2005 | |
| WO | WO-2005/072113 A2 | 8/2005 | |
| WO | WO-2005/084658 A1 | 9/2005 | |
| WO | WO-2006/072175 A1 | 7/2006 | |
| WO | WO-2007/010514 A2 | 1/2007 | |
| WO | WO-2007/010516 A2 | 1/2007 | |
| WO | WO-2007/096148 A1 | 8/2007 | |
| WO | WO-2008/094618 A2 | 8/2008 | |
| WO | WO-2009/080828 A2 | 7/2009 | |
| WO | WO-2010/063470 A2 | 6/2010 | |
| WO | WO-2010/063472 A1 | 6/2010 | |
| WO | WO-2010/091892 A2 | 8/2010 | |
| WO | WO-2010/091894 A2 | 8/2010 | |
| WO | WO-2013/012662 A2 | 1/2013 | |
| WO | WO-2013/117744 A9 | 8/2013 | |
| WO | WO-2013/156413 A1 | 10/2013 | |
| WO | WO-2013/178815 A1 | 12/2013 | |
| WO | WO-2013/178816 A1 | 12/2013 | |
| WO | WO-2014/041140 A1 | 3/2014 | |
| WO | WO-2014/041141 A1 | 3/2014 | |

OTHER PUBLICATIONS

Ameho CK et al., Prophylactic Effect of Dietary Glutamine Supplementation on Interleukin 8 and Tumor Necrosis Factor Alpha Production in Trinitrobenzene Sulphonic Acid Induced Colitis, Gut, Oct. 1997 (Oct. 1997), 41(4):487-93.

Australian Examination Report dated Jan. 31, 2014, for Application No. 2009321722 (9 pages).

Baker et al., (1962) "Potential Anticancer Agents. LXXVIII Nonclassical Antimetabolites. IV. Synthesis of Compounds Related to 4-(Iodoacetamido) Salicylie Acid, an Exo-Alkylating Irreversible Inhibitor," Journal of Organic Chemistry, 27:3283-3295.

Baz, et al. (2003) "Oxidant / Antioxidant Status in Patients with Psoriasis," *Yonsei Medical Journal* 44:(6)987-990.

Behshad et al., "A Retrospective Case Series Review of the Peroxisome Proliferator-Activated Receptor Ligand Rosiglitazone in the Treatment of Atopic Dermatitis", Arch Dermatol, 144(1):84-88 (2008).

Beilstein Database Beistein Institute zur Forderung der Chemischen Wissenschaften, Frankfurt an Main, DE XP002413839, Accession No. 2092096, J. Med. Chem., 22: 589 (1979).

Beilstein Database, Beilstein Institute for Organic Chemistry, Frankfurt an Main, DE, retrieved from XFIRE, Accession No. brn 2208094, J. Am. Chem. Soc., 68: 2335, 2338 (1946).

Beilstein Database, Beilstein Institute for Organic Chemistry, Frankfurt an Main, DE, retrieved from XFIRE, Accession No. brn 2803076, J. Org. Chem., 14: 1013, 1018 (1949).

Beilstein Database, Beilstein Institute for Organic Chemistry, Frankfurt an Main, DE, retrieved from XFIRE, Accession No. brn 3199913, Chem. Ber., 46: 3978 (1913).

Beilstein Database, Beilstein Institute for Organic Chemistry, Frankfurt an Main, DE, retrieved from XFIRE, Accession No. brn 3200601, J. Chem. Soc., pp. 104, 111 (1935).

Beilstein Database, Beilstein Institute for Organic Chemistry, Frankfurt an Main, DE, retrieved from XFIRE, Accession No. brn 3268495, Justus Liebigs Ann. Chem., 463:60 (1924).

Beilstein Database, Beilstein Institute for Organic Chemistry, Frankfurt an Main, DE, retrieved from XFIRE, Accession No. brn 3296969, Chem. News J. Ind. Sci, 36: 269 (1877).

(56) References Cited

OTHER PUBLICATIONS

Beilstein Database, Beilstein Institute for Organic Chemistry, Frankfurt an Main, DE, retrieved from XFIRE, Accession No. pcrn 859019, U.S. Pat. No. 4,429,152 A (Jan. 1984).
Beilstein Database, Beilstein Institute for Organic Chemistsry, Frankfurt an Main, DE, retrieved from XFIRE, Accession No. brn 3199917, Chem. Ber., 46: 288 (1913).
Beilstein Database, Beilstsein Institute for Organic Chemistry, Frankfurt an Main, DE, retrieved from XFIRE, Accession No. brn 3242057, Chem. Ber., 74: 500, 517 (1941).
Beilstein Database, Beistein Institut zur Forderung der Chemischen Wissenschaften, Frankfurt an Main, DE, XP002413837, Accession No. 2367395, Chem. Ber., 87: 179-181 (1954.).
Beilstein Database, Beistein Institut zur Forderung der Chemischen Wissenschaften, Frankfurt an Main, DE, XP002413838, Accession No. 2839685, J. Am. Chem Soc., 73: 903-904 (1951).
Beilstein Database, Beistein Institut zur Forderung der Chemischen Wissenschaften, Frankfurt an Main, DE, XP002413840, Accession No. 3031462, Bull Soc. Chim Belg., 61: 310-320 (1952).
Beilstein Database, Beistein Institut zur Forderung der Chemischen Wissenschaften, Frankfurt an Main, DE, XP002413842, Accession No. 3259704, Justus Liebigs Ann Chem, 429: 173 (1922).
Beilstein Database, Beistein Institut zur Förderrung der Chemischen Wisssenschaften, Frankfurt an Main, DE, XP002413836, Accession No. 1869425, J. Labelled Compd Radiopharm, 44: S225-S227 (2001).
Beilstein Database, Beisten lnsstitut zur Forderung der Chemischen Wissenschaften, Frankfurt an Main, DE, XP002413843, Accession No. 3530419, Justus Liebigs Ann Chem, 429: 164 (1922).
Beilstein Database, Beisten Institut zur Forderung der Chemischen Wissenschaften, Frankfurt an Main, DE, XP002413841, Accession No. 2641495, J. Org. Chem., 27: 3283-3295 (1962).
Bickers, et al. (2006) "Oxidative Stress in the Pathogenesis of Skin Disease," J. Investigatrive Dermatology, 126:2565-2575.
Bongartz et al., "Treatment of active psoriatic arthritis with the PPARγ ligand pioglitazone: an open-label pilot study", Rheumatology, 44:126-129 (2005).
Broadwith, P. (2009) "Enzyme Binds Both Sides of the Mirror," Chemistry World, pp. 1-2.
Brown et al., "Chimie Organique," C.R. Acad. Sc. Paris, t. (1978) 287:125-128.
Brunton, V.G., et al. (1997) "A Role of Epidermal Growth Factor Receptor, c-Src and Focal Adhesion Kinase in an in vitro Model for the Progression of Colon Cancer," Oncogene, 14: 283-293.
Bull, A.W. (2003) "The Role of Peroxisome Proliferator-Activated Receptor y in Colon Cancer and Inflammatory Bowel Disease," Arch Pathol Lab Med. 127: 1121-1123.
Clark, M., et al. (1989) "Validation of the General Purpose Tripos 5.2 Field," J. Comput Chem., 10:982-1012.
Collino et al. (2006) "Modulation of the Oxidative Stress and Inflammatory Response by PPAR-gamma Agonists in the Hippocampus of Rats Exposed to Cerebral lschemia/Reperfusion," European Journal of Pharmacology, Elsevier Science, NL, 530:70-80.
Corse et al., (1948) "Biosythesis of penicillins" J. Am. Chem. Soc., 70(9):2837-2843, XP002330829.
Database CA [Online] Chemical Abstracts Service, Columbus Ohio, US; Database Accession No. 67:50608, Abstract of Baker et al.: "Irreversible Enzyme Inhibitors. LXXXVII. Hydrophobic Bonding to dihydrofolic reductase. 9. Mode of Binding of m-aryloxyalkyl groups on, 6-diamino-1,2-dihydro-2,2-dimethyl-1-phenyl-s-triazine", (1967).
Database CA [Online] Chemical Abstracts Service, Columbus, Ohio, US, Baroni, Sergio et al., "Compounds for the selective treatment of intestinal immuninflammatory component of the celiac disease", Document No. 152:343527, Accession No. 2010:351508 CAPLUS (Giuliani International Ltd., Italy) (2007).
Database CA [Online] Chemical Abstracts Service, Columbus, Ohio, US, Database Accession No. 107:235800, Abstract of Cleary, et al., "Methylenecyclopropane rearrangement as a probe for free radical substituent effects . . . sigma . . . bul. Values for commonly encountered conjugating and organometallic groups", (1987).
Database CA [Online] Chemical Abstracts Service, Columbus, Ohio, US, Database Accession No. 111:153586, Abstract of Gonzalez, et al., ".alpha.-Amino carbanions. A second generation formamidine for facile deprotonation leading to .alpha.-quaternary substitution", (1989).
Database CA [Online] Chemical Abstracts Service, Columbus, Ohio, US, Database Accession No. 119:95018, Abstract of Yoon, et al., "Reduction of nitro compounds with borohydride exchange resin—nickel acetate", (1993).
Database CA [Online] Chemical Abstracts Service, Columbus, Ohio, US, Database Accession No. 131:144358, Abstract of Lamy-Pitara et al., "Selective Catalytic Hydrogenation of Unsaturated Derivatives of Nitrobenzene in Alcoholic Media", (1999).
Database CA [Online] Chemical Abstracts Service, Columbus, Ohio, US, Database Accession No. 50:52519, Abstract of Pratt, et al., "Reaction rates by distillation. VI. The etherification of benzyl and related alcohols", (1956).
Database CA [Online] Chemical Abstracts Service, Columbus, Ohio, US, Database Accession No. 8:526, Abstract of Schepss, "Electrolytic reduction of aldehydes", (1914).
Database CA [Online] Chemical Abstracts Service, Columbus, Ohio, US, Database Document No. 118:101608, Accession No. 1993:101608, Abstract of Breuer, et al., "An efficient synthesis of ethyl 3'-aminocinnamate", (1992).
Database CA [Online] Chemical Abstracts Service, Columbus, Ohio, US: Database Accession No. 96:19761, Abstract of Macek et al., "Studies on Local Anesthetics LXXIV. Basic esters of o-(m-) (alkoxymethyl)carbanilic acids", (1981).
Database CA [Online] Chemical Abstracts Service, Columbus, Ohio, US; Database Accession No. 105:24135, Abstract of Wulff, et al., "Chemistry of binding sites. VI. On the suitability of various aldehydes and ketones as binding sites for monoalcohols", (1986).
Database CA [Online] Chemical Abstracts Service, Columbus, Ohio, US; Database Accession No. 110:194186, Abstract of Pei et al., "A Lewis acid catalyst supported by polymers-styrene-methyl methacrylate copolymer-titanium tetrachloride complex preparation and uses in organic synthesis", (1989).
Database CA [Online] Chemical Abstracts Service, Columbus, Ohio, US; Database Accession No. 112:157479, Abstract of Joshi et al., "Catalysis by heteropoly acids: some new aspects", (1989).
Database CA [Online] Chemical Abstracts Service, Columbus, Ohio, US; Database Accession No. 121:204747, Abstract of Yang et al., "Photosolvolysis of 2-aminobenzyl alcohol in aqueous solution", (1994).
Database CA [Online] Chemical Abstracts Service, Columbus, Ohio, US; Database Accession No. 131:228419, Abstract of Engell et al., "The Decomposition of methyl hemiacetals of benzaldehyde in aqueous solution: a study of the effect of aromatic substitution", (1999).
Database CA [Online] Chemical Abstracts Service, Columbus, Ohio, US; Database Accession No. 135:180359, Abstract of Pitts et al., "Indium metal as a reducing agent in organic synthesis", (2001).
Database CA [Online] Chemical Abstracts Service, Columbus, Ohio, US; Database Accession No. 49:68907, Abstract of Mann, et al., "The action of magnesium and of Grignard reagents on certain benzyl ethers. II. The action of Grignard reagents on .omicron.-, m-, and p-(methoxy- and phenoxymethyl) anilines", (1954).
Database CA [Online] Chemical Abstracts Service, Columbus, Ohio, US; Database Accession No. 66:37529, Abstract of Minisci, et al., "Orientation in the radical amination of aromatic compounds with N-chlorodimethylamine-competition between nuclear and benzylic attack", (1966).
Database CA [Online] Chemical Abstracts Service, Columbus, Ohio, US; Database Accession No. 84:4573, Abstract of Gale, et al., "Amidomethylation of some N,N-dialkylanilines (Tscherniac-Einhorn reaction)", (1975).
Database Caplus Chemical Abstracts Service, Columbus, Ohio, US; Database Accession No. 1913:10241, Abstract of Heller: Berichte der Deutschen Chemischen Gesellschaft (1913), 46:280-294.

(56) References Cited

OTHER PUBLICATIONS

Database Caplus Chemical Abstracts Service, Columbus, Ohio, US; Database Accession No. 1949:23214, Abstract of Tomcsik et al.: Helvetica Chimica Acta (1949), 32:31-34.
Database Caplus Chemical Abstracts Service, Columbus, Ohio, US; Database Accession No. 1955:19868, Abstract of Mann et al.: Chemistry & Industry (London, United Kingdom) (1954) 373-374.
Database Caplus Chemical Abstracts Service, Columbus, Ohio, US; Database Accession No. 1979:18291, Abstract of Brown et al.: "Affinity Chromatography of L-lactate dehydrogenase (LDH) on Synthetic Supports. Preparation and Immobilization of D- and L-p-aminophenyllactic Acids, New Effectors of LDH." Comptes Rendus des Seances de l'Academic des Scie. 287(4):125-128 (1978).
Database Caplus Chemical Abstracts Service, Columbus, Ohio; Database Accession No. 1925:25469, Abstract of Sherwin: "Acetylation as a Physiologic Reaction." Proceedings of the Society for Experimental Biology and Medicine (1924), 22:182.
Database Caplus Chemical Abstracts Service, Columbus, Ohio; Database Accession No. 1967:490291, Abstract of Deljac et al.: "Absolute Configuration of (—) -β-hydroxy-β-(m-hydroxphenyl) propionic acid", Recueill des Travaux Chimiques des Pays-Bas (1967), 68(8):765-768.
Database Chemcats [Online] Chemical Abstracts Service, Columbus, Ohio, US; Accession No. 2058162244, Allichem Product List, Jun. 3, 2009; XP002591674, Feb. 6, 2008.
Database Registry (Online) Chemical Abstracts Service, Columbus, Ohio, US; Database Accession No. 1001756-73-5, Abstract & "Allichem Catalog" Jun. 3, 2009; XP002595814, Feb. 6, 2008.
Delbarre, F., et al., Chemical Abstracts, vol. 65, Columbus , Ohio, Abstract No. 93711, "Non-steroid antiinflammatory substances. I. Derivatives of the 4- and 5- aminosalicylic acids," (1964).
Deljac, A., et al., "Absolute Configuration of (−)-β-Hydroxy-β-(*m*)-Hydroxyphenyl)-Propionic Acid," Recueil des Travaux Chimiques des Pays-Bas, 86:765-768 (1967).
Dimon-Gadal et al. (2000) "Increased Oxidative Damage to Fibroblasts in Skin With and Without Lesions in Psoriasis," *Journal of Investigative Dermatology* 114:984-989.
DiPoï et al., "Epithelium-Mesenchyme Interactions Control the Activity of Peroxisome Proliferator-Activated Receptor β/δ during Hair Follicle Development", Mol. Cellular Biol., 25(5):1696-1712 (2005).
DiPoï et al., (2004) "Functions of Peroxisome Proliferator-Activated Receptors (PPAR) in Skin Homeostasis," *Lipids* 39 (11): 1093-1099.
Dubuquoy et al., "Impaired Expression of Peroxisome Proliferator-Activated Receptor Gamma in Ulcerative Colitis," Gastroenterology, 124:1265-1276 (2003).
Dubuquoy et al., "Role of peroxisome proliferator-activated receptor γ and retinoid X receptor heterodimer in hepatogastroenterological diseases," The Lancet, 360:1410-1418 (2002).
Egan et al., (2003) "Clinical pharmacology in inflammatory bowel disease: optimizing current medical therapy," *Inflammatory Bowel Disease: From Bench to Bedside, 2nd Edition*, 495-521.
Ellis et al., "Placebo Response in Two Long-Term Randomized Psoriasis Studies that were Negative for Rosiglitazone", Am J Clin Dematol 8(2):93-102 (2007).
Examination Report dated Apr. 15, 2011 for Application No. 06 766 083.7-2103 (11 pages).
Fernholz et al., (1992) "Specificity of antibody-catalyzed transesterifications using enol esters: a comparison with lipase reactions" J. Org. Chem., 57:4756-4761, XP002330828.
Fuenzalida et al., (2007) "Peroxisome Proliferator-activated Receptor Gamma Up-regulates the Bcl-2 Anti-apoptotic Protein in Neurons and Induces Mitochondrial Stabilization and Proection against Oxidative Stress and Apoptosis," J. Biol. Chem., 282(51):37006-37015.
Gampe et al., (2000) "Asymmetry in the PPARγ/RXRα Crystal Structure Reveals the Molecular Basis of Heterodimerization Among Nuclear Receptors," Mol. Cell, 5:545-555.

Gerdes, J., et al., "Growth Fractions in Breast Cancers Determined in Situ with Monoclonal Antibody Ki-67," J. Clin. Pathol., 39: 977-80 (1986).
Gormin, D., "Picosecond Transient Absorption Spectra of Aminosalicylates in Confirmation of the Triple Excitation Mechanism," J. Phys. Chem, 1989, 93, p. 5979-5980.
Guo, et al., "Effect of Uyghur Compound Xipayi Kui Jie' an on the Ultrastructure of Small Intestinal Epithelial Cell in Rat Model of Ulcerative Colitis," Journal of Xinjiang Medical University (2009) 32 (7) , p. 893-894.
Harari, P.M., "Epidermal Growth Factor Receptor Inhibition Strategies in Oncology," Endocr Relat Cancer, 11: 689-708 (2004).
Harrington et al., "A re-appraisal of lactose intolerance", Int J Clin Pract, 62(10):1541-1546 (2008).
Husova, Libuse, et al., "Hepatopathy, coeliac disease and lymphocytic colitis," Ceska A. Slovenska Gastroenterologie A. Hepatologie—Czech and Slovak Gastroenterology and Hepatology, 61 (6) (2007), 309-313.
International Preliminary Report on Patentability and Written Opinion for International Application No. PCT/EP2013/069063 dated Mar. 17, 2015 (7 pages).
International Preliminary Report on Patentability for PCT/EP13/057729 issued on Oct. 21, 2014 (6 pages).
International Preliminary Report on Patentability and Written Opinions for PCT/IE2006/000076 mailed on Jan. 22, 2008 (10 pages).
International Preliminary Report on Patentability, with Written Opinion, issued on Jan. 22, 2008, in PCT Application No. PCT/IE2006/000078 (9 pages).
International Search Report and Written Opinion for PCT/IE2006/000078, mailed Jan. 26, 2007 (14 pages).
International Search Report for PCT/EP2008/052354, mailed Jun. 9, 2008 (6 pages).
International Search Report for PCT/EP2008/068265, mailed Aug. 11, 2009 (5 pages).
International Search Report for PCT/EP2009/008631, mailed Aug. 19, 2010 (9 pages).
International Search Report for PCT/EP2009/008633, mailed Feb. 22, 2010 (4 pages).
International Search Report for PCT/EP2010/000935 mailed on Aug. 23, 2010 (5 pages).
International Search Report for PCT/EP2010/000939 mailed on Sep. 20, 2010 (5 pages).
International Search Report for PCT/EP2013/052617, mailed Aug. 12, 2014 (4 pages).
International Search Report for PCT/EP2013/057729, mailed Jun. 11, 2013 (4 pages).
International Search Report for PCT/EP2013/069062, mailed Dec. 10, 2013 (3 pages).
International Search Report for PCT/EP2013/069063, mailed Dec. 20, 2013 (3 pages).
International Search Report issued on Feb. 1, 2007 for PCT/IE2006/000076 (5 pages).
Ireland et al. (1992) "Comparison of 5-aminosalicylic acid and N-acetylaminosalicylic acid uptake by the isolated human colonic epithelial cell," *Gut* 33:1343-1347.
Janda et al., (1988) "Antibody catalysis of bimolecular amide formation" J. Am. Chem. Soc., 110:4835-4837, XP002330827.
Johnson et al., "Intestinal Fibrosis Is Reduced by early Elimination of Inflammation in a Mouse Model of IBD: Impact of a "Top-Down" Approach to Intestinal Fibrosis in Mice", Inflamm Bowel Dis, 18(3):460-471 (2012).
Jones, G., et al., "Development and Validation of a Genetic Algorithm for Flexible Docking," J. Mol. Biol., 267: 727-748 (1997).
Julien B et al., 'Antifibrogenic Role of the Cannabinoid Receptor CB2 in the Liver,' Gastroenterology, 2005, 128(3):742-55.
Kari, C., et al., "Targeting the Epidermal Growth Factor Receptor in Cancer: Apoptosis Takes Center Stage," Cancer Res., 63: 1-5 (2003).
Kloepper et al., "Immunophenotyping of the human bulge region: the quest to define useful in situ markers for human epithelial hair follicle stem cells and their niche," Experimental Dermatology, vol. 17, pp. 592-609 (2008).

(56) References Cited

OTHER PUBLICATIONS

Koeffler, H.P., "Peroxisome Proliferator-activated Receptpr γ and Cancers," Clinical Cancer Research, 9: 1-9 (2003).
Kuenzli et al., "Effect of Topical PPARβ/δ and PPARγ Agonists on Plaque Psoriasis: A Pilot Study", Dermatology, 206:252-256 (2003).
Liao, Yun-Zhang, et al., (1990) "Therapeutic Effect of Methyl 5-Aminosalicylate on Experimental Ulcerative Colitis in Rabbits," Acta Pharmacologica Sinica, 11(1): 54-56.
Lin et al., (1998) "An antibody transesterase derived from reactive immunization that utilizes a wide variety of alcohol substrates," Chem. Commun., pp. 1075-1076, XP009048652.
Lowe, D. (2009) "More Binding Site Weirdness," CORANTE: In the Pipeline, pp. 1-4.
Mager, Von P.P., et al., "Struktur-Wirkungs-Beziehungen bei Salizylsaure- und Benzoesaurederivaten," Zbl. Pharm. 118 (1979) Heft 12, p. 1259-1275.
Mangelsdorf, D.J., et al., "The Nuclear Receptor Superfamily: The Second Decade," Cell, 83: 835-839 (Dec. 1995).
Meek, W., et al., "Carboxylation of Substituted Phenols in N,N-Dimethylamide Solvents at Atmospheric Pressure," Journal of Chemical and Engineering Data, vol. 14, No. 3, 1969, p. 388-391.
Mendelsohn, J., "The Epidermal Growth Factor Receptor as a Target for Cancer Therapy," Endocr Relat Cancer, 8: 3-9 (2001).
Merck Manual Home Edition, "Ulcerative Colitis", Merck Sharp & Dohme Corp., Copyright © 2004-2011, pp. 1-6 [online] [retrieved on Apr. 19, 2013] Retrieved from http://www.merckmanuals.com/home/print/digestive_disorders/inflammatory_bowel_diseases_ibd/ulcerative_colitis.html.
Michalik, et al. (2007) "Peroxisome Proliferator-activated Receptors (PPARs) in Skin Health, Repair and Disease," *Biochimica et Biophysica Acta* 1771:991-998.
Misra, P., et al., "Phosphorylation of Transcriptional Coactivator Peroxisome Proliferator-Activated Receptor (PPAR)-Binding Protein (PBP). Stimulation of Transcriptional Regulation by Mitogen-Activated Protein Kinase," J. Biol. Chem., 277: 48745-48754 (2002).
Nolte, R.T., et al., "Ligand Binding and Co-Activator Assembly of the Peroxisome Proliferator-Activated Receptor-γ," Nature, 395: 137-143 (Sep. 1988).
O'Mahony, et al., "Coeliac Disease and Collagenous Colitis," (1990) Postgraduate Medical Journal, 66(773), pp. 238-241.
Office Action issued in Japanese Patent Application No. 2011-549494 mailed Feb. 25, 2014, and its English translation (8 pages).
Osawa, E., et al., "Peroxisome Proliferator-Activated Receptor γ Ligands Suppress Colon Carcinogenesis Induced by Azoxymethane in Mice," Gastroenterology, 124: 361-367 (2003).
Pedersen et al., "Topical rosiglitazone treatment improves ulcerative colitis by restoring peroxisome proliferator-activated receptor-gamma activity", Am J Gastroenterol, 105(7):1596-1603 (2010). Abstract only.
Pershadsingh et al., "Improvement in Psoriasis with Rosiglitazone in a Diabetic and a Nondiabetic Patient," Skinmed, vol. 4, pp. 386-390 (2005). (Abstract Only).
Peyrin-Biroulet, L., et al. (2007) "Peroxisome Proliferator-Activated Receptor Gamma Functions as an Antibacterial Factor," Journal of Crohn's and Colitis Supplements, 1(1), p. 2.
Ponchant, M., et al., Synthesis of 5-[$^{125}$I]-Iodo-Zacopride, a New Probe for 5-HT$_3$ Receptor Binding Sites, Journal of Labelled Compounds and Radiopharmaceuticals, vol. XXIX, No. 10, 1991, p. 1147-1155.
Reifen, Ram, et al. (2004) "5-ASA and Lycopene Decrease the Oxidative Stress and Inflammation Induced by Iron in Rats with Colitis," J. Gastroenterol, 39: 514-519.
Risérus, Ulf, et al., (2008) "Activation of Peroxisome Proliferator-activated Receptor (PPAR) Delta Promotes Reversal of Multiple Metabolic Abnormalities, Reduces Oxidative Stress, and Increases Fatty Acid Oxidation in Moderately Obese Men," Diabetes 57, NR. 2, 332-339.
Ritland et al., (1999) "Evaluation of 5-Aminosalicylic Acid (5-ASA) for Cancer Chemoprevention: Lack of Efficacy against Nascent Adenomatous Polyps in the Apc$^{Min}$ Mouse," Clinical Cancer Research, 5(4)855-863.
Robertson D., et al., "Structure-Activity Relationships of Arylimidazopyridine Cardiotonics: Discovery and Inotropic Activity of 2-[2-Methoxy-4-(methylsulfinyl)phenyl]-1H-imidazo[4,5-c]pyridine," J. Med. Chem. 1985, 28, p. 717-727.
Rousseaux, C., et al., Intestinal Anti-inflammatory Effect of 5-Aminosalicylic Acid is Dependent on Peroxisome Proliferator-Activated Receptor-γ, JEM 201(8): 1205-1215 (2005).
Rovner, S. (2009) "An Enzyme Reveals an Unexpected Inclusiveness, Protein Binding: Bacterial Enzyme's Active Site Welcomes Both Enantiomers of a Chiral Molecule at the Same Time," Chemical & Engineering News, pp. 1-2.
Schauber, Jurgen, et al. (2004) "Histone-Deacetylase Inhibitors Induce the Cathelicidin LL-37 in Gastrointentinal Cells," Molecular Immunology, 41(9): 847-854.
Schwab, Markus, et al. (2007) "Role of Nuclear Hormone Receptors in Butyrate-Mediated Up-Regulation of the Antimicrobial Peptide Cathelicidin in Epithelial Colorectal Cells," Molecular Immunology, 44(8): 2107-2114.
Sherwin, C.P., "Acetylation as a Physiologic Reaction," Scientific Proceedings (1924), 22, 182.
Tanaka, T., et al., "Ligands for Peroxisome Proliferator-Activated Receptors α and γ Inhibit Chemically Induced Colitis and Formation of Aberrant Crypt Foci in Rats," Cancer Res., 61: 2424-2428 (2001).
Tosti et al., "Treatment strategies for alopecia", Expert Opin Pharmacother, 10(6):1017-1026 (2009).
Tuleu, et al., "Colonic delivery of 4-aminosalicylic acid using amylose-ethyl cellulose-coated hydroxypropyl methyl cellulose capsules," Aliment Pharmacol Ther., (2002); 167: 1771-1779.
van't Riet, Bart, et al. (1979) "Synthesis of Hydroxy and Amino-Substituted Benzohydroxamic Acids: Inhibition of Ribonucleotide Reductase and Antitumor Activity," Journal of Medicinal Chemistry, 22(5):589-592.
Venkatraman et al., "Alpha-Lipoic acid-based PPARgamma agonists for treating inflammatory skin diseases", Arch Dermatol Res, 296(3):97-104 (2004). Abstract only.
Wallace JL et al., 'Inhibition of Leukotriene Synthesis Markedly Accelerates Healing in Rat Model of Inflammatory Bowel Disease,' Gastroenterology, 1989, 96(1):29-36.
Wang, R., et al., "Further Development and Validation of Emphirical Scoring Functions for Structure-Based Binding Affinity Prediction," J. Comput. Aided Mol. Des., 16: 11-26 (2002).
Wang, Tian-Tian, et al. (2004) "Cutting Edge: 1,25-Dihydroxyvitamin D3 is a Direct Inducer of Antimicrobial Peptide Gene Expression," The Journal of Immunology, 173: 2909-2912.
Westin, S., et al., "Interactions Controlling the Assembly of Nuclear-Receptor Heterodimers and Co-Activators," Nature, 395: 199-202 (Sep. 1998).
Williams, J.G., et al. (1989) "Effect of Sulphasalazine and its Active Metabolite, 5-Amino-Salicylic Acid, on Toxic Oxyden Metabolite Production by Neutrophils," Gut, 30: 1581-1587.
Wu X et al., 'Effects of Rosiglitazone on Expression of TGF-β1 in Experimental Hepatic Fibrosis Rats,' Chin J Gastroenterol Hepatol, 15(2):126-9 (2006).
Xu, H.E., et al., "Structural Determinants of Ligand Binding Selectivity Between the Peroxisome Proliferator-Activated Receptors," Proc. Natl. Acad. Sci. U.S.A., 98: 13919-13924 (2001).
Yanai, K., et al., "Para-Position Derivatives of Fungal Anthelmintic Cyclodepsipeptides Engineered with Streptomyces Venezuelae Antibiotic Biosynthetic Genes," Nature Biotechnology (2004) 22, 848-855.
Youssef, J., et al., "Role of Peroxisome Proliferator-Activated Receptors in Inflammation Control," J. Biomed Biotechnol. 3: 156-166 (2004).
Zhou et al. (1999) "Intestinal Metabolism and Transport of 5-Aminosalicylate," *Drug Metab Dispos* 27(4)479-485.
International Preliminary Report on Patentability and Written Opinion of the International Searching Authority for PCT/EP2010/000939, issued Aug. 16, 2011 (8 pages).

(56) References Cited

OTHER PUBLICATIONS

International Preliminary Report on Patentability and Written Opinion of the International Searching Authority for PCT/EP2010/000935, issued Aug. 16, 2011 (7 pages).
International Preliminary Report on Patentability and Written Opinion of the International Searching Authority for PCT/EP2009/008631, issued Jun. 7, 2011(13 pages).
International Preliminary Report on Patentability and Written Opinion of the International Searching Authority for PCT/EP2009/008633, issued Jun. 7, 2011 (6 pages).
Speca, S. et al. (2012) "Cellular and Molecular Mechanisms of Intestinal Fibrosis," World Journal of Gastroenterology 18 (28), 3635-3661.
International Preliminary Report on Patentability for PCT/EP2008/068265, completed Apr. 12, 2010 (11 pages).
International Preliminary Report on Patentability for PCT/EP2008/052354, completed May 22, 2009 (20 pages).
International Preliminary Report on Patentability and Written Opinion for International Application No. PCT/EP2013/052617 dated Aug. 12, 2014 (5 pages).
International Preliminary Report on Patentability and Written Opinion for International Application No. PCT/EP2013/069062 dated Mar. 17, 2015 (7 pages).
Written Opinion of the International Searching Authority for PCT/EP2008/052354 mailed Jun. 9, 2008 (10 pages).
Written Opinion of the International Searching Authority for PCT/EP2008/068265 mailed Aug. 11, 2009 (12 pages).
Yu J et al., 'Peroxisome Proliferator-Activated Receptors Gamma Reverses Hepatic Nutritional Fibrosis in Mice and Suppresses Activation of Hepatic Stellate Cells in vitro,' Int J Biochem Cell Biol, Jun 2010 (Jun. 2010) Feb. 13, 2010 (Feb. 13, 2010)(ePub), 42(6):948-57.
Azhar S, 2010, 'Peroxisome Proliferator-Activated Receptors, Metabolic Syndrome and Cardiovascular Disease,' Future Cardiol, 6(5):657-91 (NIH Public Access Author Manuscript).
Brown and Joyeau, (1979), 'Use of p-Aminophenyl D and L-Lactic Acids and p-Aminophenyl Pyruvic Acid as Effectors in the Affinity Chromatography of Lactate Dehydrogenase,' Biochimie, 61(3):437-42 (Abstract only).
Casen Recordati Group, (2016), 'Cleen Ready-to-Use Enema, Summary of Product Characteristics Updated Jun. 16, 2016,' emc+, medicines.org.UK/emc, XP-002763390, <https://www.medicines.org.UK/emc/print-document?documentId=542>, [retrieved Oct. 25, 2016] (5 pages).
Casen Recordati Group, (2016), 'Cleen Ready-to-Use Enema,' emc+, medicines.org.UK/emc, XP-002763391, <https://www.medicines.org.UK/emc/history/542#version 9>, [retrieved Oct. 25, 2016] (2 pages).
Floch and White, (2006), 'Management of Diverticular Disease is Changing,' World J Gastroenterol, 12(20):3225-8.
Karnik et al., (2009) 'Hair Follicle Stem Cell-specific *PPARγ*Deletion Causes Scarring Alopecia,' J Invest Dermatol, 129(5):1243-57.
Lees et al., (2008) 'Analysis of Germline GLI1 Variation Implicates Hedgehog Signalling in the Regulation of Intestinal Inflammatory Pathways,' PLoS Med, 5(12):e239 (15 pages).
Medline Database, U.S. National Library of Medicine, Bethesda, MD, XP002763389, Accession No. NLM23651165, Benjamin B et al., (2013) 'PPAR-gamma in Ulcerative Colitis: A Novel Target for Intervention,' Curr Drug Targ, 14(12):1501-7.
Peyrin-Biroulet et al., (2010), 'Peroxisome Proliferator-Activated Receptor Gamma Activation is Required for Maintenance of Innate Antimicrobial Immunity in the Colon,' Proc Natl Acad Sci USA, 107(19):8772-7.
Porter and Ihrig, (1923), 'Asymmetric Dyes,' J Am Chem Soc, 45(8):1990-3 (Abstract only).
Ramprasad et al., (2002) 'Sustained-Delivery of Apolipoprotein E-peptidomimetic Using Multivesicular Liposomes Lowers Serum Cholesterol Levels,' J Control Release, 79(1-3):207-18.
Result Summary for Study ID No. SB-999910/150 (2002) "A study in patients with Crohn's Disease to evaluate the effect of AVANDIA™ on inflammatory activity mediated by monocytes/macrophages" Retrieved from: download.gsk-clinicalstudyregister.com/files/23093.pdf on May 23, 2012 (2 pages).
Rousseaux et al., (2010), 'Preclinical and Toxicological Assessments of the Novel Orally Bioavailable PPAR Ligand GED-0507-34-Levo for the Treatment of Inflammatory Bowel Disease,' Gastroenterology 2010 DDW Abstract Supplement, AGA Abstract #1080, 138(5-Suppl 1):S-157.
Rousseaux et al., (2011) 'Preclinical Evaluation of Intestinal Anti-Inflammatory/Analgesic Properties and Phase I Clinical Trial of a New PPAR Agonist Ged-0507-34-Levo,' Gastroenterology, 140(5):S-515 (Abstract).
Tursi et al., (2002), 'Long-Term Treatment with Mesalazine and Rifaximin Versus Rifaximin Alone for Patients with Recurrent Attacks of Acute Diverticulitis of Colon,' Digest Liver Dis, 34(7):510-5.
Tursi, (2004), 'Acute Diverticulitis of the Colon—Current Medical Therapeutic Management,' Exp Opin Pharmacother, 5(1):55-9.
Wei et al., (2010) 'Peroxisome Proliferator-Activated Receptor γ: Innate Protection from Excessive Fibrogenesis and Potential therapeutic Target in Systemic Sclerosis,' Curr Opin Rheumatol, 22(6):671-6 (HHS Public Access version of Author Manuscript).
Written Opinion of the International Searching Authority for International Application No. PCT/EP2013/052617 mailed Aug. 12, 2014 (4 pages).
Written Opinion of the International Searching Authority for International Application No. PCT/EP2013/069062 mailed Dec. 10, 2013 (6 pages).

\* cited by examiner

```
GTAATTTATTTTACTTCTGTGTCCTAAGGGTAATTTCTCAGGATTGTTTTCAAATTGCTTTTTTAGGGGAAATAGGTCAT
TTGCTATATTACAAGCAATCCCCAAATTTTATGGTCTTCCAGGAAAAGTTATTACCGTTTATGATACTAACAGTTCCTGA
GACTTAGCTATGATCAGTATGTTCATGAGGTGGAGCAGTTCCTGTGTTGCAGCTTTTAACAACAGATGGCATTCATTAAA
TCACAAAGTATGTTAAAGGTCACAAAAGCAAAATAACTGTCTGAGGCTAAGGCCCACGTGGGACAGTCTAATACCCATGA
GTACTCAACTTGCCTTGATGTCTGAGCTTTCCAGTGCAATGTGAATTTGAGCAGCCAGAAATCTATTAGTAGAAAGCAAG
ACAGATTAATATAGGTTAAAACAATGATTTAAATATGTTTCTCCCAATAATTATCTCTTTCCCTGGAATCAACTTGTATG
AAACCTTGTCAAAATGTACTCCACAAGTATGTACAATTAAGTATTTTAAAAATAAATGGCAAACATTAAAAACAAGAGTG
AATACTCAAGTAGATTTGTCATGGGATTTTTATAAGAAGACTGGTATCAGGTAATGTATCTTTAAAGACTAGGCTGCTCT
GCTGACGTAGTAACCATTTTTTATTCCTTTACTTTCCTAATAGCCTTGCTTTCACTTAAGAAAAAAAAAGGCTAGGCACG
GTGGCTCACGCCTGTAATCCCAGCACTTTGGGAGGCCAAGGTGAGTAGATCACCTGAGGTCAGGAGTTCGAGACAAGCCT
GGCCAACGTGGAGAAAACCTGTCTCTACTAAAAGTACAAAAATTAGCCAGGCATGGTGGTGGGCACCTGTAATCCCAGCT
ACTCAGGAGGTTGAGGCAGGAGAATTGCTTGAACCCAAGAGGTGGAAGTTGCAGTGAGCTGAGATCATGCCACTGCCCTC
CAGCTTGGGCGGCAACAACAACAACAAAAAAAGATTCCCAGGCTTCACCCTCTACAGTCTATGGAAAGTCATGGGAGTCT
ATTAAAAAAAAACAGACACTATAAACCAAATTAAAAGATGGGAAAATTTTTCTATCACGTTTTAATATGTGATATCCAAA
CTCCCATTAAGAATTTTTATATCAGTAATAAGATAAAACTCAGAAGAAAAATGCCCAATTAACAAGAAGAGCTTCACCTC
TTAAATAATCAGAAAAAGAAAAGCACATAATATTTACGTCAAAGTATCAAAAATGTAAAAGTTTTATAATAGGCATTAGC
AAGGCAGACGGATACAGGCACACATCTAACTCTATGTAGGATTTAACTTGGAAGACAATTTGCATTTCAATCAATCAAAA
ACCATTTTTTTTTTTGAGATGATCTCCCTGTGTTGCCCAGACTGGCCTCAAGCTCCTGGGCTTGAGCAGTCCTACAGTCT
GAGCCTCCAAAAGTACTGGCAAAACAGGCGTGATTGACCATGCCCAGCCTGTATATAAGGATATTCATTTGCAGCATTGT
TTGCAACACAAAAATGTAAAACCAACCGGTGTTTAATATGCAAGATGTTAATTTATGGTACATTCTTGCTGTGGAAAGCT
ATGCATCTGTTAGAGGTGGGTCTATATGTTCTGATACAGGCAGAACTCTAAGAGCTATTAAGTGAAGAAAAGGCTGAAAA
TACATATGGCATAATTCCATATATGTTAAATTGTTCTATATTTTAAATGTTATACACGTTTCCATTTGTATTTACGTAAT
AATAATGATCCCTGAGCTGTACTGTTGTATACATGCTACAAGAAAGACCCATTTAATCCCCACAGCCTATGATGAATTAT
CCACATTCTACAGGTGACAAAATAGAGGCACAAAGTTAAGTAATTTTTGTCAGGTGAGATTTAAACCCAGGCATTCTGAC
TCCTGTATAACCATTAAGATATGCAGAGAAAGAAAACTGGAAAGATACATATTGCTGAAGATACTTATTATAGGAAGAGG
AGGGGGGAGGGTGAAGGAATTTGCAAGTTTTTCATAGATGTTTCCATATTGTTTGAATCTCTTACAAAATATGTTCAGCA
TATTTTTAAAGAGAAAATTTGGGGCAAAATACTTATTTTTGTATTATGTAAACAAATTTTAAAATAATGTGTGGCTGGGT
GCGCTGGCTCACACCTGTAATCCCAACACTTTAGGAGGCTGAGGCAAGAGGATTGCTTGAGCCCAGGAGTTCAAGACCAG
CCTGGGTGACATGGCAAAACTCCATCTCTACTAAAAATACAAAAAATTAGCCAGTCGTGGTGGCGCACACCTATGGTCCC
ACCTACCCAGGATGCTGAGATGGGAGGATCACTTGAGCCCAGGAAGTCAAGGCTGCAGGAAGCTGTGATCGCACCACTGC
ACTCCCACCTGGGCAACAGAGTGAGACCCGGTCACCAAAAAACAAAAAAAACAAAAAAAATTGGTAATCGTTTTCTTCAG
ACATTTTCCGGGTTCCTCTGCTTAACTTGTATAGGAAGTCTGAGGTTTTTGTGTTGGTCTTTACCTTTTTTTTTTTTTTT
TTTTTTTAAGATGGAGTCTCATTCTGTTGCCCAGGCTGGAGTGCAGTGGCATGATCTTGGCTCCTGCAACCTCCGCCTCC
TGGGTTCAAGTGATTCTCCTGCCTCAGCCTCCTGAGTAGCCGGGACTACAGGCGCATGCCACGATGCCTGGCTAATTTTT
TGTATTTTTAGTAGAGATGGGGTTTCACCATGTTAGCTAGGACGGTCTCGATCTCCTGACCTCGTGATCCGCCCACCTCG
GCCTCCCAAAGTGCTGGAATTACAGGTGTGAGCCACCACGCCCGGCCCTGATCTTTACATTTTTAAATATTGCATTAGTG
AACCGTGTACTGATTTTGTGATCATAGATAACCCAGTTAAATATTAAGTCTTAATTATCACTTAGTATTTTACAACCTCA
GTTGCAGTTATAAAGTAAGGGTTCCACATACCTCCTAACAgttcctagaaaa
```

METHODS OF TREATING LACTOSE INTOLERANCE

RELATED APPLICATIONS

This application is the U.S. national stage of International (PCT) Patent Application No. PCT/EP2013/057729, filed Apr. 12, 2013, and published under PCT Article 21(2) in English, which claims priority to EP12425073.9, filed Apr. 18, 2012, and U.S. Provisional Application No. 61/672,931, filed Jul. 18, 2012, both of which are incorporated by reference in their entireties.

BACKGROUND

Lactase protein is a disacharidase (β-galactosidase) expressed on the tips of the villi of the small intestine having the ability to hydrolyze lactose into galactose and glucose. Inadequate lactase-phlorizin hydrolase (LPH) activity is responsible for lactose intolerance/malabsorption leading to diarrhea, abdominal pain or bloating after lactose ingestion. Primary lactase deficiency (or lactase non persistence or hypolactasia) is the main cause of lactose intolerance, due to the relative or absolute absence of lactase expression in the small bowel, occurring in childhood at various ages and in different racial groups Approximately 70% of the world's population has primary lactase deficiency. The percentage of lactose deficiency varies according to ethnicity and is related to the use of dairy products in the diet reaching up to 20% of North European, 40% of Mediterranean European, 80% of Africans, and 90% of Asian population. Typical treatments for lactose intolerance is lactose exclusion (leading to nutritional impairment) or expansive regimen such as the use of lactose deficient milk or lactase supplementation.

It has been reported that two particular Single Polymorphisme (SNP) nucleotide are tightly associated with adult-type hypolactasia. A C at position$_{-13910}$ ($C_{-13910}$) upstream of the lactase gene is 100% associated and a G at position$_{-22018}$ ($G_{-22018}$) is more than 95% associated with lactase non-persistence in the Finnish population. SNP. Expression of LPH mRNA in the intestinal mucosa in individuals with $T_{-13910}$ and $A_{-22018}$ is higher than found in individuals with $C_{-13910}$ and $G_{-22018}$, suggesting a transcriptional regulation of LPH gene. However, much of the regulation of the LPH gene remains unknown. Accordingly, effective agents, that are useful in the treatment of lactose intolerance and related disorders are needed.

Peroxisome Proliferator Activated Receptors (PPARs) are members of the nuclear hormone receptor super family, which are ligand-activated transcription factors regulating gene expression. PPARs play a role in the regulation of cell differentiation, development and metabolism of higher organisms.

Three types of PPAR have been identified: alpha, expressed in the liver, kidney, heart and other tissues and organs, beta/delta expressed for example in the brain, and gamma, expressed in three forms: gamma1, gamma2, and gamma3. PPARγ receptors have been associated with stimulation of keratinocyte differentiation, and has served as a potential drug target for a number of disease states including skin disorders such as psoriasis and atopic dermatitis.

SUMMARY

This disclosure is generally directed methods of treating, ameliorating or substantially preventing lactose intolerance in a patient need thereof, comprising administering a composition that includes a PPAR modulater, e.g. PPARα, δ or γ, e.g., a PPARγ modulator, e.g., agonist (e.g. such as a compound disclosed herein) to a patient in need thereof. Also provided herein is a method for stimulating lactose gene expression in a patient in need thereof, comprising administering a PPAR agonist, e.g., a PPAR α, δ, or PPARγ agonist to the patient.

Also provided herein is a method for treating diarrhea, abdominal pain and/or bloating after lactose ingestion in a patient in need thereof, comprising administering a PPAR agonist, e.g. a PPARα, PPARδ, PPARγ agonist. For example, provided herein is a method for ameliorating lactose intolerance in a patient ingesting a composition that includes lactose, comprising administering a PPAR agonist before, substantially simultaneously with, or after said ingestion.

BRIEF DESCRIPTION OF THE FIGURES

FIG. 5: Identification of direct repeats in the promoter (3000 pb) of the human Lactase gene (SEQ ID NO: 3). DR1 are in bold, and DR2 are in bold and start with "AG". Also indicated are TATA box and lowercases letters represent the beginning of the first exon.

DETAILED DESCRIPTION

Figure 1:
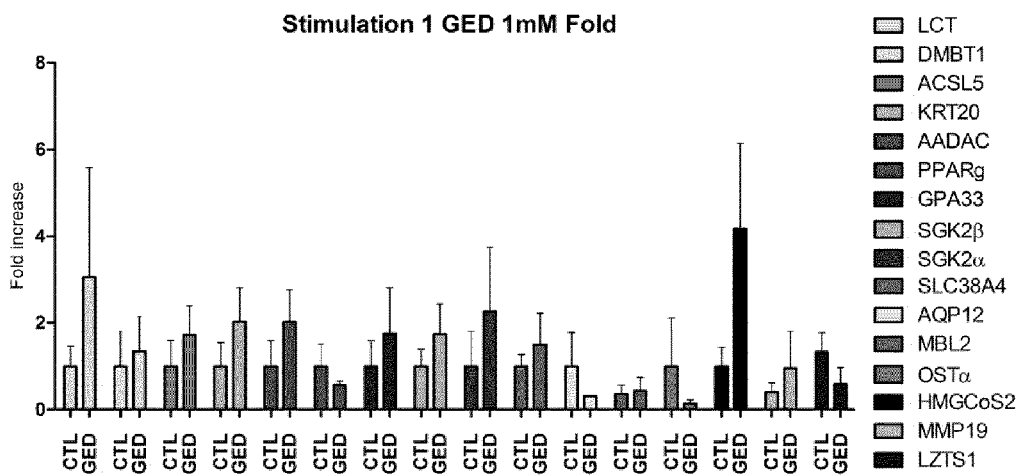
FIG. 1A depicts gene expression evaluated in qPCR in synchronized Caco2 cells after 24 hours of treatment by compound 34, 1 mM. Confirmation of the 12 up-regulated genes expression observed in microarrays. Up regulated expression of AQP12, OSTα and LZTS1 are not confirmed. Results are expressed in fold compared to control (set to value 1).
FIG. 1B depicts gene expression evaluated in qPCR in synchronized Caco2 cells after 24 hours of treatment by compound 34, 1 mM. Confirmation of the 12 up-regulated genes expression observed in microarrays. Up regulated expression of AQP12, OSTα and LZTS1 are not confirmed. Results are expressed in relative expression.
Figure 1:
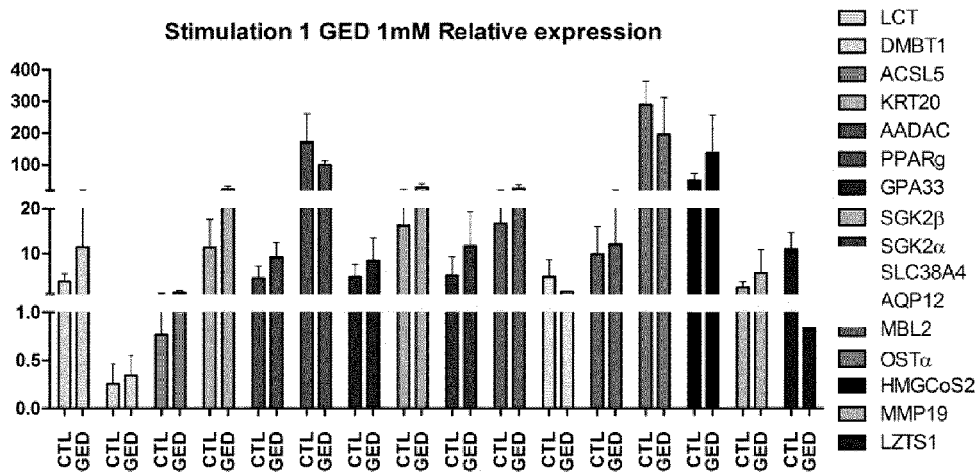

The features and other details of the disclosure will now be more particularly described. Before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

DEFINITIONS

"Treating" includes any effect, e.g., lessening, reducing, modulating, or eliminating, that results in the improvement of the condition, disease, disorder and the like.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$alkenyl, $C_2$-$C_{10}$alkenyl, and $C_2$-$C_6$alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, etc.

The term "alkoxy" as used herein refers to an alkyl group attached to an oxygen (—O-alkyl-). Exemplary alkoxy groups include, but are not limited to, groups with an alkyl, alkenyl or alkynyl group of 1-12, 1-8, or 1-6 carbon atoms, referred to herein as $C_1$-$C_{12}$alkoxy, $C_1$-$C_8$alkoxy, and $C_1$-$C_6$alkoxy, respectively. Exemplary alkoxy groups include, but are not limited to methoxy, ethoxy, etc. Similarly, exemplary "alkenoxy" groups include, but are not limited to vinyloxy, allyloxy, butenoxy, etc.

The term "alkyl" as used herein refers to a saturated straight or branched hydrocarbon, such as a straight or branched group of 1-12, 1-10, or 1-6 carbon atoms, referred to herein as $C_1$-$C_{12}$alkyl, $C_1$-$C_{10}$alkyl, and $C_1$-$C_6$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc. In certain embodiments, alkyl refers to $C_1$-$C_6$ alkyl. In certain embodiments, cycloalkyl refers to $C_3$-$C_6$cycloalkyl.

Alkyl, alkenyl and alkynyl groups can, in some embodiments, be optionally be substituted with or interrupted by at least one group selected from alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl.

The term "alkynyl" as used herein refers to an unsaturated straight or branched hydrocarbon having at least one carbon-carbon triple bond, such as a straight or branched group of 2-12, 2-8, or 2-6 carbon atoms, referred to herein as $C_2$-$C_{12}$alkynyl, $C_2$-$C_8$alkynyl, and $C_2$-$C_6$alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl, etc.

The term "aryl" as used herein refers to refers to a mono-, bi-, or other multi-carbocyclic, aromatic ring system. In certain embodiments, aryl refers to a monocyclic and/or bicyclic, 5 to 6 membered ring. The aromatic ring may be substituted at one or more ring positions with substituents selected from alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, and/or aryls. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl.

The term "carboxy" as used herein refers to the radical —COOH or its corresponding salts, e.g. —COONa, etc.

The term "cycloalkyl" as used herein refers to a monovalent saturated or unsaturated cyclic, bicyclic, or bridged bicyclic hydrocarbon group of 3-12, 3-8, 4-8, or 4-6 carbons, referred to herein, e.g., as "$C_{4-8}$cycloalkyl," derived from a cycloalkane. Exemplary cycloalkyl groups include, but are not limited to, cyclohexanes, cyclohexenes, cyclopentanes, cyclopentenes, cyclobutanes and cyclopropanes. Cycloalkyl groups may be substituted with alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. Cycloalkyl groups can be fused to other cycloalkyl, aryl, or heterocyclyl groups. In certain embodiments, cycloalkyl refers to $C_3$-$C_6$ alkyl.

The terms "halo" or "halogen" or "Hal" as used herein refer to F, Cl, Br, or I.

The term "haloalkyl" as used herein refers to an alkyl group substituted with one or more halogen atoms.

The term "phenyl" as used herein refers to a 6-membered carbocyclic aromatic ring. The phenyl group can also be fused to a cyclohexane or cyclopentane ring. Phenyl can be substituted with one or more substituents including alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include to any animal, including mammals, preferably mice, rats, other rodents, rabbits, dogs, cats, swine, cattle, sheep, horses, or primates, and most preferably humans. The compounds of the invention can be administered to a mammal, such as a human, but can also be other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in whom modulation of PPAR receptors is desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system, animal or human that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount which results in the prevention of or a decrease in the symptoms associated with a disease associated with PPAR receptors.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well known asymmetric synthetic methods.

Geometric isomers can also exist in the compounds of the present invention. The symbol ═══ denotes a bond that may be a single, double or triple bond as described herein. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a polymorph. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the e.g., Examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms, such as through hydrolysis in blood. For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as ($C_1$-$C_8$) alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

Similarly, if a compound of the invention contains an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate).

If a compound of the invention incorporates an amine functional group, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl or natural α-aminoacyl-natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$)alkyl and Y$^3$ is ($C_1$-$C_6$)alkyl, carboxy ($C_1$-$C_6$)alkyl, amino($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino, morpholino, piperidin-1-yl or pyrrolidin-1-yl.

PPAR modulators

The disclosure provides, at least in part, compounds having PPAR modulating activity, e.g., PPARγ modulating activity. Such compounds, may, for example, be represented by formulas depicted below. Also contemplated herein are compositions that include a compound represented by the disclosed formulas and e.g., a pharmaceutically or cosmetically acceptable carrier or excipient.

For example, in an embodiment, contemplated PPAR modulating compounds (e.g. compounds having PPAR activity) may be represented by:

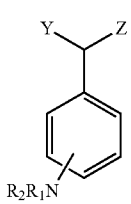

(I)

and pharmaceutically acceptable salts, stereoisomers, prodrugs thereof, wherein:

$R_1$ and $R_2$, are each independently selected from the group consisting of H and $C_{1-6}$ alkyl; or $R_1$ and $R_2$ together with the nitrogen atom they are bonded to form an aromatic or aliphatic ring with 5 or 6 atoms which may be optionally substituted;

Y and Z are each independently selected from the group consisting of H, OH, COOH, —OR$_3$, —CH(OR$_3$)COOH; and $R_3$ is selected from the group consisting of H, phenyl, benzyl, vinyl, allyl, $C_{1-6}$ alkyl or $C_{1-6}$ alkyl substituted by one, two, three or more halogens.

In an embodiment, Y may be H or COOH. For example, Y may be H and Z may be CH(OR$_3$)COOH, or Y may be COOH and Z may be —OR$_3$. In some embodiments, $R_3$ may be methyl, ethyl, n-propyl, or isopropyl.

In other embodiments, the NR$_1$R$_2$ moiety may be in the 4' position or may be in the 3' position. In certain embodiments, $R_1$ and $R_2$ are H.

Exemplary compounds also include those represented by formulas IIa or IIb or a pharmaceutically acceptable salt, enantiomer or stereoisomer of:

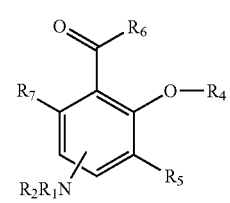

(IIa)

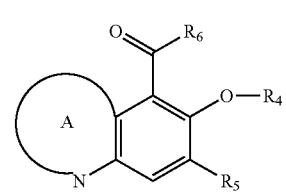

(IIb)

wherein:

$R_1$ and $R_2$ are each independently selected from the group consisting of H and $C_{1-6}$ alkyl; or $R_1$ and $R_2$ together, with the nitrogen atom they are bonded to, form an aromatic or aliphatic ring with 5 or 6 atoms;

$R_6$ is selected from the group consisting of: —NHOH, OH, and —OR$_9$;

$R_9$ is $C_{1-6}$ alkyl;

$R_4$ is selected from H, phenyl, benzyl, vinyl, allyl, $C_{1-6}$ alkyl or $C_{1-6}$ alkyl substituted by one or more halogens;

$R_5$ and $R_7$ are each independently hydrogen or halo; or $R_4$ and $R_5$, or $R_4$ and $R_6$ together, form a fused heterocyclic ring with 5 or 6 atoms, optionally substituted with halo or $C_{1-6}$ alkyl; and A is a fused heterocyclic ring; or a pharmaceutically acceptable salt thereof.

In certain embodiments, the $NR_1R_2$ moiety of formula IIa may be in the 4' position or may be in the 3' position. In certain embodiments, $R_1$ and $R_2$ are H.

$R_9$, in some embodiments, may be methyl, ethyl, n-propyl, or isopropyl.

In some embodiments a compound can be represented by

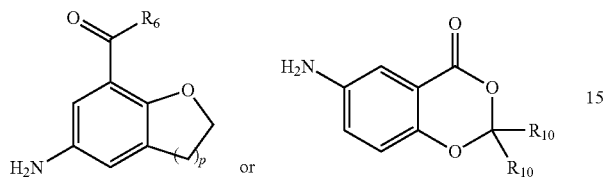

wherein p is 1 or 2, $R_6$ is OH or —$OR_9$, wherein R9 is defined above, and $R_{10}$, independently for each occurrence, is selected from the group consisting of H, halo, or $C_{1-6}$ alkyl, e.g. methyl or ethyl.

Exemplary compounds contemplated herein include:

(II)

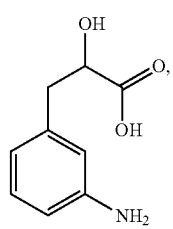

(III)

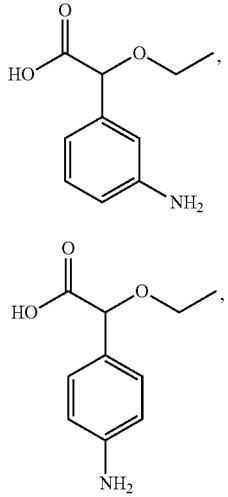

(IV)

(V)

(VI)

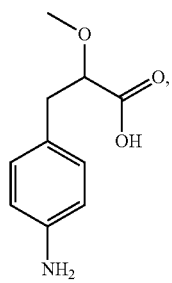

(VIII)

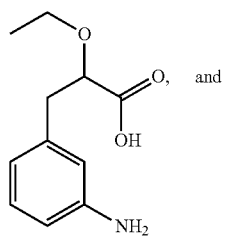
and (IX)

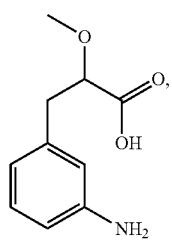

or a pharmaceutically acceptable salt thereof.

In some embodiments, contemplated compounds include: 4-amino-N-hydroxy-2-methoxybenzamide (compound 13); 6-methoxy quinoline-5-carboxylic acid (compound 36); 6-methoxy-1,2,3,4-tetrahydroquinoline-5-carboxylic acid (compound 37); 5-diisopropylaminosalicylic acid (compound 38).

Other exemplary compounds include those represented by:

(compound 13):

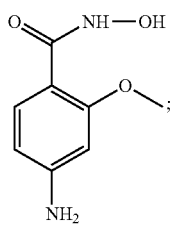

(compound 14):

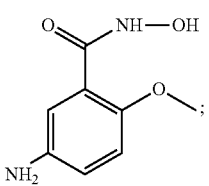

(compound 26):

(compound 17):

(compound 31):

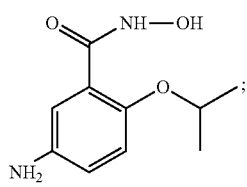

(compound 28):

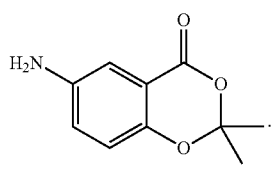

Compounds contemplated herein include racemic mixtures, and enantiomers of compounds, for example: (±)-2-hydroxy-3-(3'-aminophenyl) propionic acid (compound 20); (±)-2-methoxy-2-(4'-aminophenyl) acetic acid (compound 23); (±)-2-ethoxy-2-(3'-aminophenyl) acetic acid (compound 32); (±)-2-ethoxy-2-(4'-aminophenyl) acetic acid (compound 33); (±)-2-methoxy-3-(4'-aminophenyl) propionic acid (compound 34) "±34" (racemic form); (±)-2-ethoxy-3-(4'-aminophenyl) propionic acid (compound 39); (±)-2-ethoxy-3-(3'-aminophenyl) propionic acid (compound 40).

For example, the compounds used in the methods of the present invention can be enantiomers of the following racemic mixtures: (R,S)-2-hydroxy-2-(3-aminophenyl)acetic acid (compound 10); (R,S)-2-hydroxy-2-(4-aminophenyl)acetic acid (compound 11); (R,S)-2-hydroxy-3-(4'-aminophenyl)propionic acid (compound 21); (R,S)-2-methoxy-2-(3'-aminophenyl)acetic acid (compound 22); (R,S)-2-methoxy-3-(3'-aminophenyl)propionic acid (compound 35); (R,S)-2-methoxy-3-(4-aminophenyl)propionic acid (compound 34), as well as enantiomers, e.g.: (+) 2-S-methoxy-3-(4-aminophenyl)propionic acid (compound 34); (−) 2-R-methoxy-3-(4-aminophenyl)propionic acid (compound 34).

Other racemic type mixtures of compounds contemplated include: e.g. (±)-2-hydroxy-2-(3'-aminophenyl)acetic acid (compound 10); (±)-2-hydroxy-2-(4'-aminophenyl)acetic acid (compound 11); (±)-2-hydroxy-3-(4'-aminophenyl)propionic acid (compound 21) and (±)-2-methoxy-2-(3'-aminophenyl)acetic acid (compound 22).

Further compounds contemplated for use in the disclosed methods: 5-aminosalicylo-hydroxamic acid (compound 5); 3-dimethylaminosalicylic acid (compound 6); 2-methoxy-4-aminobenzoic acid (compound 7); 2-methoxy-5-aminobenzoic acid (compound 8); 5-methylaminosalicylic acid (compound 9); 4-methylaminosalicylic acid (compound 12); 4-acetylaminosalicylic acid (compound 16); 2-ethoxy-4-aminobenzoic acid (compound 18); 2-ethoxy-5-aminobenzoic acid (compound 19); 4-dimethylaminosalicylic acid (compound 24); 2-ethoxy-4-aminobenzoylhydroxamic acid (compound 25); 6-hydroxyquinoline-5-carboxylic acid (compound 27); 2-(2-propyl)oxy-4-aminobenzoic acid (compound 30); 4-(1-piperazinyl)salicylic acid (compound 41); (R,S) 5-oxa-quinoline-6-carboxylic acid (compound 15); 6-methoxy quinoline-5-carboxylic acid (compound 36); 6-methoxy-1,2,3,4-tetrahydroquinoline-5-carboxylic acid (compound 37); 5-diisopropylaminosalicylic acid (compound 38); and 4-diisopropylaminosalicylic acid (compound 42).

Methods for making contemplated compounds may be found for example in WO2007/010516 and WO2007/010514, each hereby incorporated by reference in their entirety.

Also provided herein are compounds represented by:

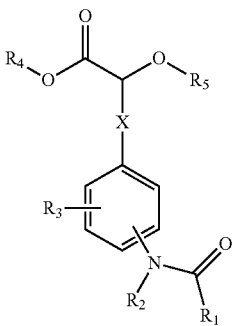

wherein X is $C_1$-$C_3$alkylene, optionally substituted with one, two or three substituents selected from halogen or hydroxyl;

$R_1$ is selected from the group consisting of $C_1$-$C_6$alkyl, $C_3$-$C_6$cycloalkyl, $C_2$-$C_6$alkenyl, and $C_2$-$C_6$alkynyl;

$R_2$ is selected from the group consisting of hydrogen and $C_1$-$C_6$alkyl;

$R_3$ is independently selected, for each occurrence from the group consisting of hydrogen, $C_1$-$C_6$alkoxy, $C_1$-$C_6$alkyl, cyano, $C_3$-$C_6$cycloalkyl, halogen, hydroxyl, and nitro;

$R_4$ is selected from the group consisting of hydrogen and $C_1$-$C_6$alkyl;

$R_5$ is $C_1$-$C_6$alkyl;

or pharmaceutically acceptable salts or N-oxides thereof.

In one embodiment, $R_1$ can be $C_1$-$C_6$alkyl, such as methyl. In one embodiment, $R_2$ can be hydrogen. In another embodiment, $R_3$ can be selected from the group consisting of hydrogen, $C_1$-$C_6$alkyl, halogen, and hydroxyl. In a further embodiment, $R_3$ can be hydrogen. In one embodiment, $R_4$ and $R_5$ can each be $C_1$-$C_6$alkyl. In another embodiment, $R_4$ may be hydrogen and $R_5$ may be methyl. In one embodiment, X may be $(CH_2)_n$, wherein n is 1 or 2, such as 1.

In another embodiment, —$NR_2$—$COR_1$ can be in the meta position relative to X as shown in formula III'.

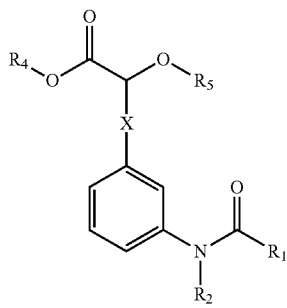

III'

In another embodiment, —NR$_2$—COR$_1$ can be in the para position relative to X as shown in formula IV'.

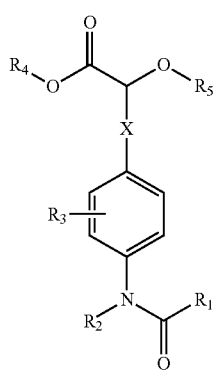

IV'

The disclosure provides, at least in part, compounds represented by formula II', as depicted below. Also contemplated herein are compositions that include a compound represented by formula II and e.g., a pharmaceutically acceptable carrier.

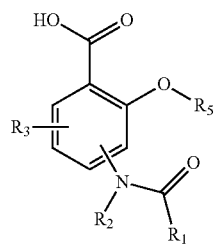

II' wherein R$_1$ is selected from the group consisting of C$_1$-C$_6$alkyl, C$_3$-C$_6$cycloalkyl, C$_2$-C$_6$alkenyl, and C$_2$-C$_6$alkynyl;

R$_2$ is selected from the group consisting of hydrogen and C$_1$-C$_6$alkyl;

R$_3$ is independently selected, for each occurrence from the group consisting of hydrogen, C$_1$-C$_6$alkoxy, C$_1$-C$_6$alkyl, cyano, C$_3$-C$_6$cycloalkyl, halogen, hydroxyl, and nitro;

R$_5$ is hydrogen or C$_1$-C$_6$alkyl;

or pharmaceutically acceptable salts or N-oxides thereof.

Compounds of Formula II' are also contemplated as shown below, as well as compositions that include a compound represented by formula II' and e.g., a pharmaceutically acceptable carrier. Contemplated compounds can include:

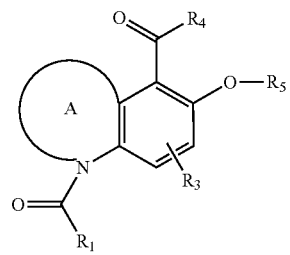

V' wherein R$_1$ is selected from the group consisting of C$_1$-C$_6$alkyl, C$_3$-C$_6$cycloalkyl, C$_2$-C$_6$alkenyl, and C$_2$-C$_6$alkynyl;

R$_3$ is independently selected, for each occurrence from the group consisting of hydrogen, C$_1$-C$_6$alkoxy, C$_1$-C$_6$alkyl, cyano, C$_3$-C$_6$cycloalkyl, halogen, hydroxyl, and nitro;

R$_4$ is selected from the group consisting of hydrogen and C$_1$-C$_6$alkyl;

R$_5$ is hydrogen or C$_1$-C$_6$alkyl; and

A is a fused five or six membered heterocycle;

or pharmaceutically acceptable salts or N-oxides thereof.

In one embodiment, R$_1$ can be C$_1$-C$_6$alkyl, such as methyl. In another embodiment, R$_1$ and R$_3$ can each be C$_1$-C$_6$alkyl, such as methyl. In one embodiment, R$_2$ can be hydrogen.

In some embodiments, a compound can be represented by

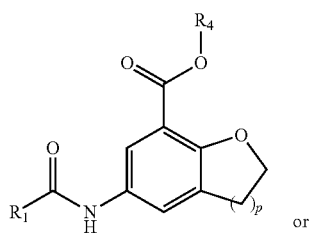

VI' or

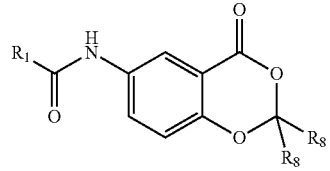

VII' wherein p is 1 or 2;

R$_1$ is selected from the group consisting of C$_1$-C$_6$alkyl, C$_3$-C$_6$cycloalkyl, C$_2$-C$_6$alkenyl, and C$_2$-C$_6$alkynyl;

R$_4$ and R$_8$ are each independently selected from the group consisting of hydrogen and C$_1$-C$_6$alkyl;

or pharmaceutically acceptable salts or N-oxides thereof.

Contemplated compounds, and pharmaceutical compositions, comprising at least one compound, may be selected from the group consisting of: N-acetyl-(R)-(−)-3-(4-aminophenyl)-2-methoxypropionic acid (Compound A), N-acetyl-(S)-(−)-3-(4-aminophenyl)-2-methoxypropionic acid (Compound B), racemic N-acetyl-(S)-(−)-3-(4-aminophenyl)-2-methoxypropionic acid (compound AB);

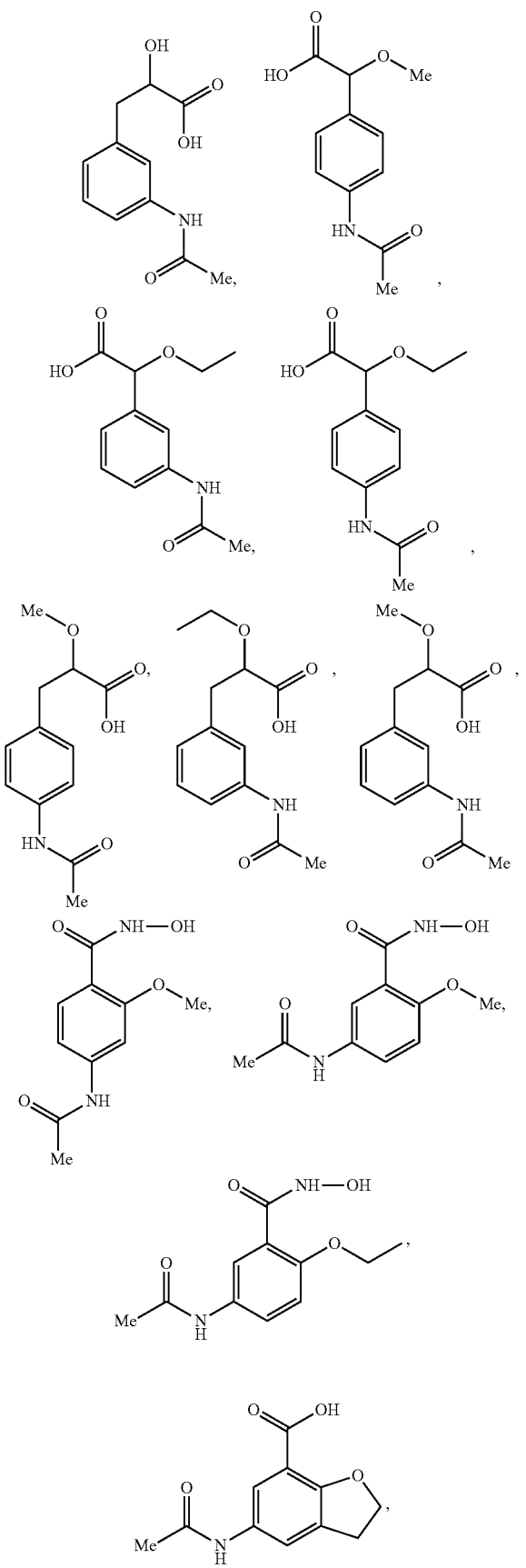

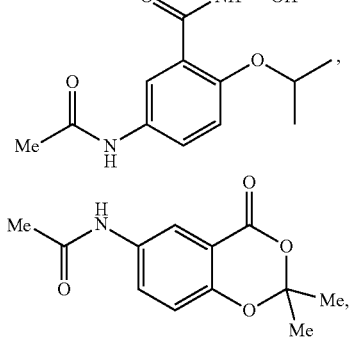

4-acetamino-N-hydroxy-2-methoxybenzamide; 1-acetyl-6-methoxy-1,2,3,4-tetrahydroquinoline-5-carboxylic acid, 5-acetamido-2hydroxybenzoic acid (e.g., acetalyated 5-aminosalicyclic acid) or pharmaceutically acceptable salts or N-oxides thereof.

Also provided herein are other PPAR modulator or agonists including 5-amino salicyclic acid (mesalamine), sulfasalazine, pioglitazone, rosiglitazone, pomegranate flower extract, non-steroidal anti inflammatories including ibuprofen, and Ψ-baptigenin.

The present disclosure also provides pharmaceutical compositions comprising compounds as disclosed herein formulated together with one or more pharmaceutically or cosmetically acceptable carriers. These formulations include those suitable for oral, rectal, topical, buccal and parenteral (e.g., subcutaneous, intramuscular, intradermal, or intravenous) administration, or for topical use, e.g. as a cosmetic product. Although the most suitable form of administration in any given case will depend on the degree and severity of the condition being treated and on the nature of the particular compound being used.

Therapeutic Applications

The disclosure is directed at least in part to treating or ameliorating lactose intolerance using a PPAR modulator, e.g., a PPARγ modulator, such as a disclosed compound. For example, methods of treating diarrhea, abdominal pain and/or bloating after lactose ingestion is provided, wherein a disclosed compound (or e.g., a composition that includes a disclosed compound) is administered to a subject in need thereof, e.g. orally administered.

For example, provided herein is a method for ameliorating lactose intolerance in a patient ingesting a composition that includes lactose, comprising administering a PPAR agonist, e.g., a PPARα, PPARδ, and/or a PPARγ agonist before, substantially simultaneously with, or after said ingestion.

Also contemplated herein are compositions used for reducing lactose intolerance, e.g. a disclosed composition may form part of, or is used for making, a low lactose content milk or milk product, comprising a PPAR modulator. Such compositions may be part of a whey, a milk or a cheese.

The compounds of the invention may be administered to subjects (animals and/or humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

Generally, a therapeutically effective amount of active component will be in the range of from about 0.1 mg/kg to about 100 mg/kg, optionally from about 1 mg/kg to about 100 mg/kg, optionally from about 1 mg/kg to 10 mg/kg. The amount administered will depend on variables such as the type and extent of disease or indication to be treated, the overall health status of the particular patient, the relative biological efficacy of the compounds, formulation of compounds, the presence and types of excipients in the formulation, and the route of administration. The initial dosage administered may be increased beyond the upper level in order to rapidly achieve the desired blood-level or tissue level, or the initial dosage may be smaller than the optimum and the daily dosage may be progressively increased during the course of treatment depending on the particular situation. Human dosage can be optimized, e.g., in a conventional Phase I dose escalation study designed to run from 0.5 mg/kg to 20 mg/kg. Dosing frequency can vary, depending on factors such as route of administration, dosage amount and the disease condition being treated. Exemplary dosing frequencies are once per day, once per week and once every two weeks.

Contemplated formulations or compositions comprise a disclosed compound and typically may also include a pharmaceutically acceptable carrier or excipient.

Contemplated compositions may be administered by various means, depending on their intended use, as is well known in the art. For example, if compositions of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or enemas or suppositories. For application by the ophthalmic mucous membrane route, compositions of the present invention may be formulated as eyedrops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose vary depending upon the subject being treated, and the particular mode of administration.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, film-coated tablets, sugar-coated tablets, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of or consist of, the recited processing steps. Except where indicated otherwise, the order of steps or order for performing certain actions are immaterial so long as the invention remains operable. Moreover, unless otherwise noted, two or more steps or actions may be conducted simultaneously.

EXAMPLES

The compounds disclosed herein can be prepared in a number of ways well known to one skilled in the art of organic synthesis.

Example A

Materials and Methods

Cell Culture

Caco-2 colonic adenocarcinoma cell lines were used. Caco-2 cells grew in Dulbecco's modified Eagle's medium (DMEM, Invitrogen, Cergy-Pontoise, France) supplemented with 20% foetal calf serum (FCS, Dutscher, Brumath, France), 1% penicillin-streptomycin (5 ml/l) (Invitrogen) and 1% non-essential amino acids (5 ml/l) (Invitrogen). All cell lines were cultured as confluent monolayers at 37° C. in a controlled, 5% $CO_2$ atmosphere. Each week, the confluent monolayer were trypsinized (Invitrogen) and then replated after a 1:10 dilution. For the stimulation experiments, cells were placed in 6-well plates at a density of $1 \times 10^6$ cells per well. Serum deprivation was used 16 hours prior to stimulation in order to synchronize the cells.

Treatment of the Cells

The cells were treated with Compound 34 (1 mM and 30 mM), 5-ASA (30 mM), or pioglitazone (1 µM). When necessary, the vehicle DMSO (Sigma) is used as control (Ctrl). After 24 hrs of stimulation, the wells were rinsed three times with sterile PBS at 4° C. The cells were then lysed with lysis buffer (RA1, Macherey-Nagel) containing 1% β-mercaptoethanol. The plates were frozen at −80° C. for subsequent RNA extraction. A time course experiment consisting of stimulation of Caco-2 cells by compound 34, 1 mM during 6 hrs and 12 hrs was also done in order to compare gene expression according treatment duration.

RNA Extraction

Total RNA were extracted with a Nucleospin RNA kit (Macherey-Nagel, Hoerdt, France). After RNAse inactivation, the total RNA was cleaned of trace genomic DNA via a DNAse treatment and eluted in RNAse-free, DEPC-free water. The purity of the RNA will be evaluated by UV spectroscopy on a Nanodrop system from 220 to 350 nm. Before microarray experiment, RNAs were also profiled on an Agilent 2100 bioanalyzer. One µg of total RNA were used in the microarray analysis (minimum concentration: 50 ng/µl).

Microarrays

Dual-colour gene expression microarrays were used compare the cRNA from the samples (cells treated with DMSO (Ctrl) vs. cells treated with an agonist (Ago)). Briefly, the RNA from the samples is first reverse-transcribed into cDNA (Affinity-Script RT, Agilent), which is then used as the substrate for the synthesis and amplification of cRNA by T7 RNA polymerase in the presence of cyanine 3-CTP for the Ctrl sample (green fluorescence) and cyanine 5-CTP for the Ago sample (red fluorescence). The two labelled cRNAs were then mixed and hybridized on the same array (G4851A Agilent 8x44K), which is then scanned (with an Agilent G2505B scanner). The fluorescence was visualised after laser excitation and the relative intensities of the two fluorophores will be expressed as a ratio, in order to yield the over- or under-expression status of each gene (using Gene-Spring software (Agilent)). This analysis was performed for each agonist. The transcriptomic profiles obtained for each agonist were then compared. Expression of genes of interest was quantified by quantitative PCR, in order to confirm the microarray results.

Quantitative PCR

Transcripts of genes were estimated by quantitative PCR (qPCR) in order to confirm microarrays results. 1 µg of total RNA was reverse-transcripted into cDNA using the High Capacity cDNA Achive kit (Applied biosystems). qPCR was performed using an ABI PRISM 7000 sequence detection system (Applied Biosystem). Primer pairs for each transcript were chosen with qPrimer depot software. Quantification of qPCR signals was performed using ΔCt relative quantification method using GAPDH as a reference gene. The values were represented in terms of relative quantity of mRNA level variation or fold increase compared to control conditions.

Generation of PPARγ Knock Down Cells

PPARγ knock down IECs were obtained using the pSU-PER.retro system (OligoEngine). Forward and reverse target sequences corresponding to nucleotides 105-123 of the human PPARg mRNA (5-'-GCCCTTCACTACTGTTGAC-3' (SEQ ID NO: 1)) were cloned into the BglII/XhoI restriction sites of the pSUPERretro vector (pRS) giving the ShPPAR construct. A negative control pRS plasmid containing the sequence 5'-ACGCTGAGTACTTCGAAAT-3' (SEQ ID NO: 2) targeted against the luciferase gene was also generated (ShLuc construct). Both constructions were transfected in Caco-2 cells using Nucleofector technology from Amaxa Biosystems, according to the manufacturer's protocol. Stably transfected clones were selected 24 h post-transfection with complete culture medium supplemented with puromycin (5 µg/ml). The silencing of PPARg expression was checked by quantitative RT-PCR and western-blot analysis. Once established, ShPPAR and ShLuc cell lines were maintained in complete medium supplemented with 2.5 µg/ml puromycin.

Example 1

Microarray

In order to evaluate the feasibility of transcriptomic analysis of intestinal epithelial cells stimulated with the PPAR agonist compound 34, the gene expression profile of Caco-2 cells only stimulated with compound 34 at the concentration of 1 mM was compared. Cell stimulations were done with 4 replicates and a total of 44 000 genes were screened. 52 genes showed a significant different expression in the compound 34, 1 mM condition in comparison with controls ($p<0.05$)(Table 1). 49 genes were up-regulated in the compound 34, 1 mM condition in comparison with controls (one gene (LCT 1) with a fold change superior of 5, four genes with a fold change between 3 and 5, and 13 genes with a fold change between 2 and 3 (Table1). Three genes were down-regulated in the compound 34, 1 mM condition in comparison with controls (MYB, OXA13 and ANKRD1).

TABLE 1

Comparison of transcriptomic profiles in epithelial cells treated by compound 34 1 mM versus control. Results are expressed in fold.

| Gene Symbol | Description | Fold change | Regulation |
|---|---|---|---|
| LCT | *Homo sapiens* lactase | 5.2924175 | up |
| DMBT1 | *Homo sapiens* deleted in malignant brain tumors 1, transcript variant 2 | 3.8939168 | up |
| KRT20 | *Homo sapiens* keratin 20 | 3.1442842 | up |
| AADAC | *Homo sapiens* arylacetamide deacetylase (esterase) | 3.0116935 | up |
| MBL2 | *Homo sapiens* mannose-binding lectin 2 | 2.8058631 | up |
| GPA33 | *Homo sapiens* glycoprotein A33 | 2.662811 | up |
| SLC38A4 | *Homo sapiens* solute carrier family 38, member 4, transcript variant 1 | 2.6554945 | up |
| C11orf86 | *Homo sapiens* chromosome 11 open reading frame 86 | 2.583426 | up |
| SGK2 | *Homo sapiens* serum/glucocorticoid regulated kinase 2, transcript variant 1 | 2.5728035 | up |
| MMP19 | *Homo sapiens* matrix metallopeptidase 19, transcript variant 1 | 2.481643 | up |
| OSTalpha | *Homo sapiens* organic solute transporter alpha | 2.4348273 | up |
| LZTS1 | *Homo sapiens* leucine zipper, putative tumor suppressor 1 | 2.3766112 | up |
| HMGCS2 | *Homo sapiens* 3-hydroxy-3-methylglutaryl-Coenzyme A synthase 2, transcript variant 1 | 2.231923 | up |
| PLIN2 | *Homo sapiens* perilipin 2 | 2.2110133 | up |
| CREB3L3 | *Homo sapiens* cAMP responsive element binding protein 3-like 3 | 2.1615057 | up |
| SLC23A3 | *Homo sapiens* solute carrier family 23 (nucleobase transporters), member 3 transcript variant 1 | 1.9120694 | up |
| ACSL5 | *Homo sapiens* acyl-CoA synthetase long-chain family member 5 | 1.8756381 | up |
| HIGD1A | *Homo sapiens* HIG1 hypoxia inducible domain family, member 1A | 1.8233925 | up |
| MUC17 | *Homo sapiens* mucin 17, cell surface associated | 1.79823 | up |
| AGPAT2 | *Homo sapiens* 1-acylglycerol-3-phosphate O-acyltransferase 2 | 1.7209687 | up |
| FABP1 | *Homo sapiens* fatty acid binding protein 1, liver | 1.7156018 | up |
| AQP12A | *Homo sapiens* aquaporin 12A | 1.7124082 | up |
| DNAH12 | *Homo sapiens* dynein, axonemal, heavy chain 12 | 1.7119135 | up |
| COL16A1 | *Homo sapiens* collagen, type XVI, alpha 1 | 1.7069026 | up |
| SLC25A42 | *Homo sapiens* solute carrier family 25, member 42 | 1.697567 | up |
| AQP12B | *Homo-sapiens* aquaporin-12B | 1.6971904 | up |
| ITIH3 | *Homo sapiens* inter-alpha (globulin) inhibitor H3 | 1.6908818 | up |
| EMP1 | *Homo sapiens* epithelial membrane protein 1 | 1.6551878 | up |
| CAPS | *Homo sapiens* calcyphosine, transcript variant 1 | 1.645898 | up |
| ACSM3 | *Homo sapiens* acyl-CoA synthetase medium-chain family member 3 transcript variant 2 | 1.6409295 | up |
| SLC46A1 | *Homo sapiens* solute carrier family 46, member 1 | 1.6296347 | up |
| ABCG2 | *Homo sapiens* ATP-binding cassette, sub-family G, member 2 | 1.6244398 | up |
| MYB | *Homo sapiens* v-myb myeloblastosis viral oncogene homolog (avian) transcript variant 2 | 1.6136038 | down |
| COL12A1 | *Homo sapiens* collagen, type XII, alpha 1, transcriptvariant long | 1.5990913 | up |
| CYP2B6 | *Homo sapiens* cytochrome P450, family 2, subfamily B, polypeptide 6 | 1.5909243 | up |
| MMP19 | *Homo sapiens* matrix metallopeptidase 19 transcript variant 1 | 1.5854398 | up |
| CREB3L3 | *Homo sapiens* cAMP responsive element binding protein 3-like 3 | 1.578399 | up |
| ANKRD1 | *Homo sapiens* ankyrin repeat domain 1 | 1.5722646 | down |
| ZNF575 | *Homo sapiens* zinc finger protein 575 | 1.5662627 | up |
| SLC25A20 | *Homo sapiens* solute carrier family 25 (carnitine/acylcarnitine translocase), member 20 | 1.563665 | up |
| GALNT2 | *Homo sapiens* UDP-N-acetyl-alpha-D-galactosamine:polypeptide N-acetylgalactosaminyltransferase 2 | 1.5570259 | up |
| RHOU | *Homo sapiens* ras homolog gene family, member U | 1.5535966 | up |
| SLC46A1 | *Homo sapiens* solute carrier family 46, member 1 | 1.5489862 | up |
| PPARGC1B | Peroxisome proliferator-activated receptor gamma coactivator 1-beta | 1.5455792 | up |
| CHST3 | *Homo sapiens* carbohydrate (chondroitin 6) sulfotransferase 3 | 1.5176716 | up |
| HOXA13 | *Homo sapiens* homeobox A13 | 1.5115318 | down |
| HIGD1A | *Homo sapiens* HIG1 hypoxia inducible domain family, member 1A, transcript variant 3 | 1.5103043 | up |
| ACSL4 | *Homo sapiens* acyl-CoA synthetase long-chain family member 4, transcript variant 1 | 1.5066991 | up |
| LUM | *Homo sapiens* lumican | 1.5007194 | up |

Confirmation by qPCR

We used quantitative PCR to confirm microarrays results. We quantified by quantitative PCR the expression of the 15 most up regulated genes evaluated by microarrays (SGK2 alpha, SGK2 beta, GPA33, CKT 20, LCT1, AADAC, DMBT1, ACSL5, MMP19, SLC28A4, AQP12, MBL2, OSTalpha, HMGCoAS2, LZTS1) in Cacao2 cells cultured in the same condition. Data obtained by quantitative PCR and presented in the FIGS. 1a-b confirmed μarray results for the 12/15 up regulated genes except for AQP12, OST α and LZTS1.

Figure 2:
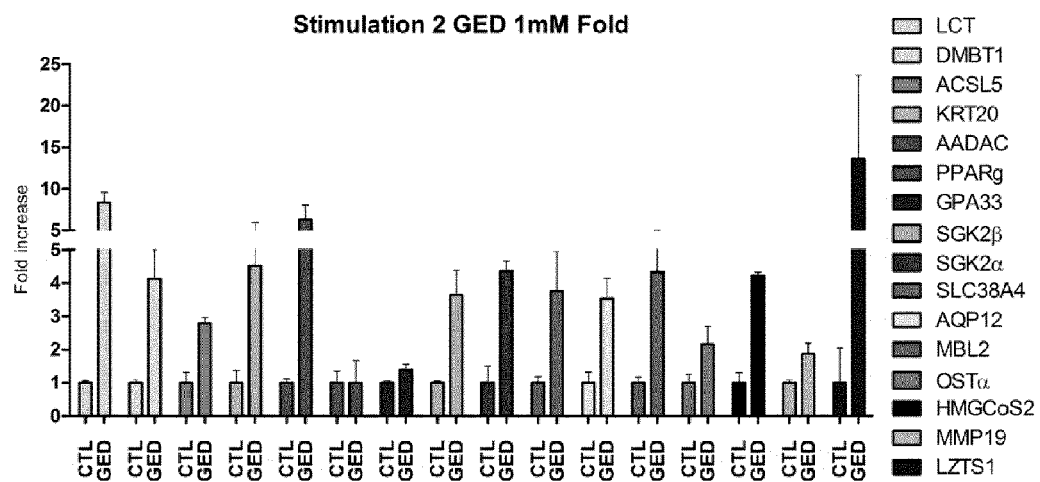
FIG. 2A depicts gene expression evaluated in qPCR in synchronized Caco2 cells after 24 hours of treatment by compound 34, 1 mM. Confirmation of all the 15 up-regulated genes expression observed in microarrays. Results are expressed in fold, compared to control (set to value 1).
FIG. 2B depicts gene expression evaluated in qPCR in synchronized Caco2 cells after 24 hours of treatment by compound 34 1 mM. Confirmation of all the 15 up-regulated genes expression observed in microarrays. Results are expressed in relative expression.
Figure 2:
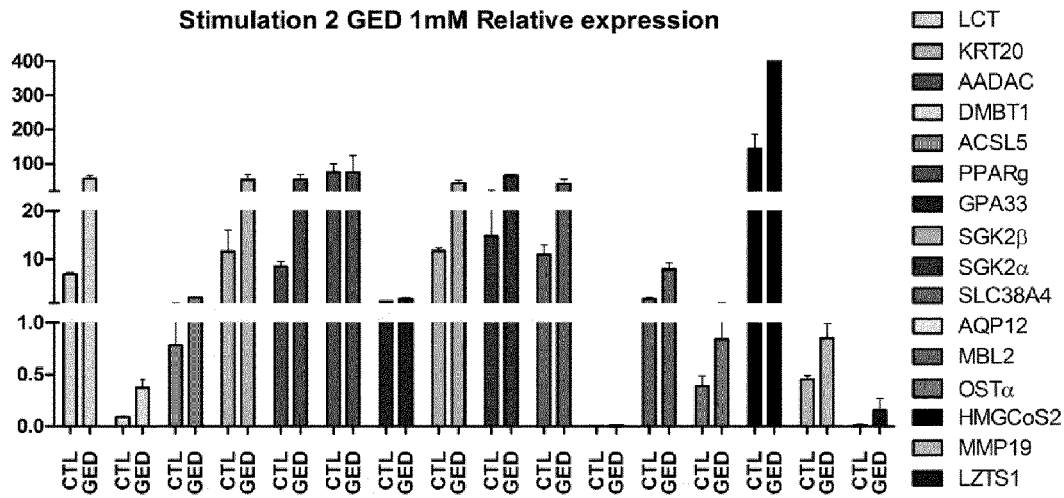

Genes variations were evaluated with a second and independent experiment in stimulated Caco-2 cells. The same stimulation protocol was used (compound 34 1 mM vs control) and gene expressions were studied using qRT-PCR. We confirmed the up-regulation of all the selected genes induced by compound 34 (including AQP12, OSTa and LZTS1 which are weakly expressed but upregulated by compound 34) except for GPA33 (FIGS. 2A and 2B).

Interestingly, in this experiment, PPARγ mRNA expression was not modified following compound 34 treatment supporting that compound 34 mediated upregulated target genes was mainly due to the modulation of PPARγ activity by compound 34, rather than an increased of the receptor expression.

Correlation Between Gene Expression Expressed in Fold in Microarrays and qPCR

Figure 3:
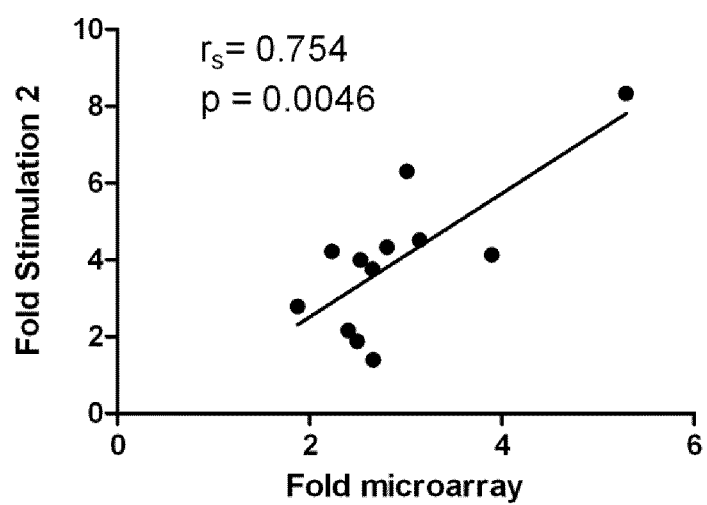
FIG. 3 depicts gene expression expressed in fold, of stimulation 2 are correlated of stimulation 1 microarrays results (r=0.754, p=0.0046).

To evaluate more definitively the reproducibility of our microarray data, we evaluated the correlation between quantitative PCR evaluation and microarray analysis. We confirmed a significant strong correlation between microarrays (stimulation 1) and qPCR (stimulation 2) results expressed in Fold Change (r=0.754, p=0.0046) (FIG. 3).

Example 2

Lactase Gene as a (PPAR) Target Gene

Among the new 15 new target genes of compound 34 expressed by epithelial cells, the gene encoding for lactase was one with the strongest induction (fold change 5.29). This induction was confirmed in the second stimulation suggesting that the lactase gene is one of the most PPARg-sensitive genes in our analysis (FIG. 2a). Due to the functional consequences of lactase gene abnormalities in lactose deficiency, a common disorder found in 20% of European population, we decided to deeper characterize this result. Inadequate lactase-phlorizin hydrolase (LPH) activity is responsible of lactose intolerance/malabsorption leading to diarrhea, abdominal pain or bloating after lactose ingestion.

Figure 4:
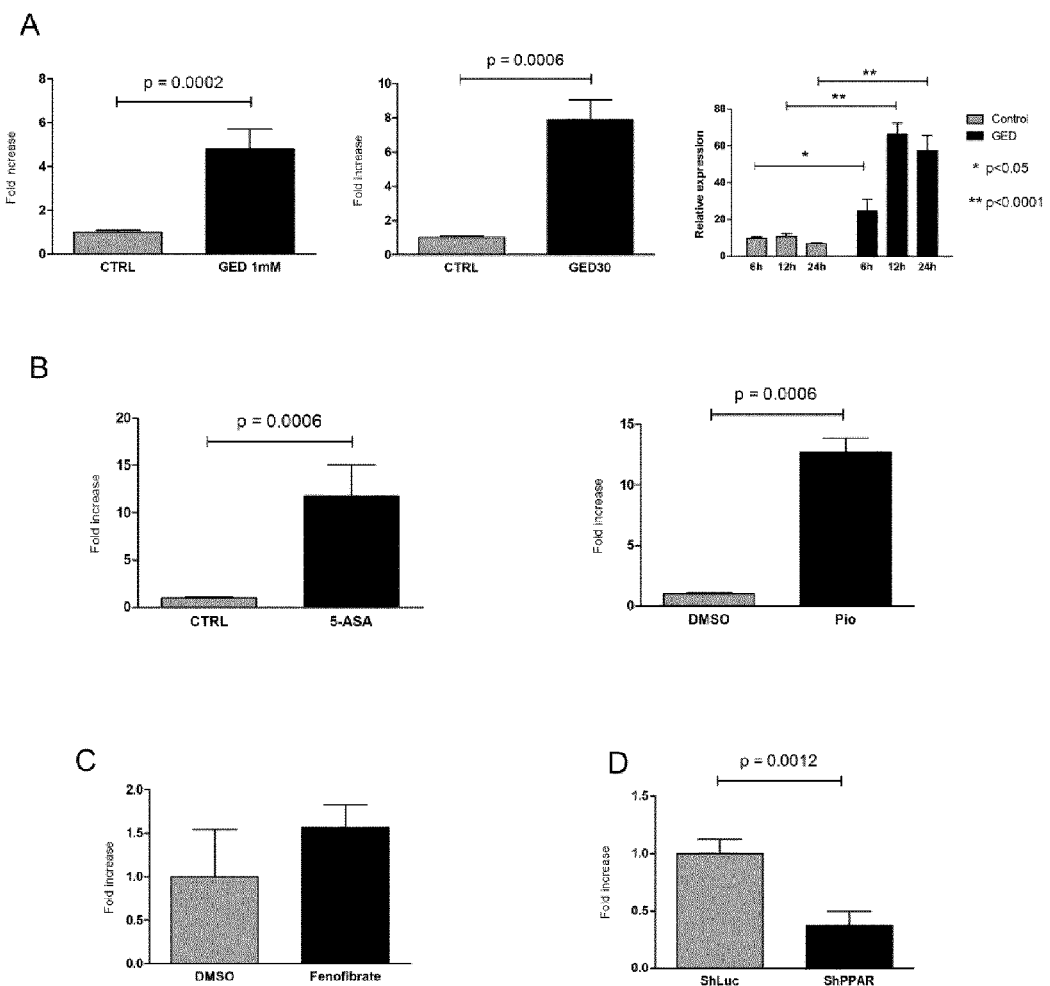
FIG. 4 shows that Lactase mRNA expression is induced by PPAR. Caco-2 cells were stimulated with various PPARγ and PPARα agonists. Statistical differences were analyzed with GraphPad software using a non-parametric Mann-Whitney test.

FIG. 4 shows the results of lactase transcript expression in different experiments of Caco-2 cells stimulated with various agonists of PPAR. Each experiment has been done at least twice. The lactase gene expression was first confirmed to be stimulated by compound 34 at two different concentrations (1 mM, fold increase 4.78, p=0.0002; 30 mM, fold increase 7.9, p=0.0006) (FIG. 4A). Time course experiment showed that 6 hours of stimulation by compound 34 1 mM is enough to significantly increase Lactase mRNA expression (p<0.05) and that the maximum expression is reached at 12 hours of treatment (p<0.0001) (FIG. 4A). Similarly to compound 34, 5ASA 30 mM and pioglitazone 1 µM, significantly increased similarly lactase mRNA expression (FIG. 4B)(respectively 12.69 fold increase, p=0.0006, 11.76 fold increase, p=0.0006). Fenofibrate, a PPARα agonist, induced weakly and without significancy the lactase gene expression in Caco-2 cells (FIG. 4C). In Caco2 ShPPAR cell line, a cell line stably expressing a short hairpin anti-sense RNA against PPAR leading to a specific 70% down expression of PPARg expression, and lactase mRNA expression is significantly reduced by 63% (p=0.0012) compared to ShLuc control cells (FIG. 4D). Altogether, these data demonstrated that the human lactase gene is inducible by PPAR agonists in Caco-2 cells and that Lactase gene could be a new PPAR target gene in intestinal epithelial cells.

Presence of PPRE Sequences at 3000 bp Upstream the LCT Gene

PPARγ is able to bind DNA as a heterodimer with another nuclear receptor RXR. The heterodimer PPARγ-RXR recognizes short dimeric palindromic sequences (consensus AGGTCA or TGACCT) spaced by one or two nucleotides giving the DR1 (direct repeat 1) or DR2 (direct repeat 2) thereby defining the PPARγ response element (PPRE). To better evaluate the potential regulation of the LCT gene by PPAR, we investigated the potential presence of PPRE sequences upstream the LCT gene. Bioinformatics tools were used to find PPRE in the human Lactase gene. Three different programs were used: NUBIScan, PPRE Search and MatInspector FIG. 5 represents the result of the in silico analysis of the 3000 bases pair upstream of the transcription start point of the human Lactase gene. Only direct repeats that were predicted by at least two different programs are indicated. This analysis revealed that the 3000 bp upstream of the transcription start site contain several PPRE which could be used by PPAR to regulate Lactase expression.

Transcriptomic analysis of intestinal epithelial cells has been found to be stimulated by compound 34 1 mM using microarray showing a significant modification of 52 genes. These results were confirmed using quantitative RT-PCR in different and independent experiments. Among these 52 genes, we focused of interest on the gene encoding for lactase and confirmed upregulated LCT gene expression by 5.29. 5-ASA and pioglitazone are also able to enhance LCT gene expression in Caco2 cells, the spontaneous level of LCT gene expression is significantly reduced by 70% in PPARγ deficient epithelial cells compared to control epithelial cells, 5ASA and pioglitazone kept their upregulatory effects on LCT gene expression in PPAR semi deficient epithelial cells, suggesting that impaired expression of LCT gene may be restored by PPAR agonists. Altogether, these data demonstrate that PPAR may be a new modulator of LCT gene expression and suggest that PPAR agonist and particularly a new class of PPARg agonist targeting the gut may be a new strategy to treat patients with lactase deficiency.

Example 3

Reporter Gene Assay and Chromatin Immunoprecipitation Experiments

The 3000 bp of the lactase gene promoter in the pGL4-Luc reporter vector was cloned. This construction (and the control empty vector) is transiently transfected in Caco-2 cells. The cells are then treated with various PPAR agonists and the luciferase activity is measured in order to evaluate the regulation of lactase promoter activity by PPAR modulators. The identification and localization of the PPAR response element(s) is achieved by successive deletions of the promoter region cloned in the pGL4-Luc reporter vector. The physical binding of PPARg on the promoter of the Lactase gene is studied by ChIP experiments in Caco-2 cells stimulated or not with PPAR agonists.

Example 4

PPARγ Agonists Ability to Modulate (to Increase) Lactase Activity

Both stimulation of Caco-2 cells and ex-vivo stimulation of small pieces of mice intestine are used to test whether PPARγ agonists are able to increase lactase activity. The lactase activity (disaccharidase activity) is assessed with o-nitrophenyl-β-D galactoside (ONPG) as a substrate. Upon hydrolysis of the β-galactosidic bond, ONPG yields galactose and o-nitrophenol, a yellow compound which can be detected by spectrophotometric methods (absorption max=450 nm). Alternatively, the expression level of lactase gene in the intestine of mice is evaluated which will receive compound 34 or 5-ASA per os.

REFERENCES

All publications and patents mentioned herein, including those items listed below, are hereby incorporated by reference in their entirety as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A method for treating and/or ameliorating lactose intolerance or lactase deficiency in a patient in need thereof, comprising administering an effective amount of a PPARγ agonist compound to said patient, wherein the PPARγ agonist is represented by Formula I:

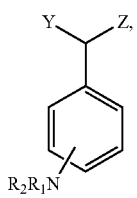

or a pharmaceutically acceptable salt, an N-oxide, and/or a stereoisomer thereof, wherein:

$R_1$ and $R_2$, are each independently selected from the group consisting of H and $C_{1-6}$ alkyl; or $R_1$ and $R_2$ together with the nitrogen atom they are bonded to form an aromatic or aliphatic ring with 5 or 6 atoms which may be optionally substituted;

Y and Z are each independently selected from the group consisting of H, OH, COOH, —$OR_3$, —$CH(OR_3)$COOH; and $R_3$ is selected from the group consisting of H, phenyl, benzyl, vinyl, allyl, $C_{1-6}$ alkyl or $C_{1-6}$ alkyl substituted by one, two, three or more halogens.

2. The method of claim 1, wherein the PPARγ agonist is selected from the group consisting of: (±)-2-hydroxy-3-(3'-aminophenyl) propionic acid; (±)-2-methoxy-2-(4'-aminophenyl) acetic acid; (±)-2-ethoxy-2-(3'-aminophenyl) acetic acid; (±)-2-ethoxy-2-(4'-aminophenyl) acetic acid; (±)-2-methoxy-3-(4'-aminophenyl) propionic acid; (±)-2-ethoxy-3-(4'-aminophenyl) propionic acid; (±)-2-ethoxy-3-(3'-aminophenyl) propionic acid, and (R,S)-2-methoxy-3-(4-aminophenyl)propionic acid, or a pharmaceutically acceptable salt thereof.

3. The method of claim 1, wherein the PPARγ agonist is (R)-2-methoxy-3-(4-aminophenyl) propionic acid or a pharmaceutically acceptable salt thereof.

4. A method for treating and/or ameliorating lactose intolerance or lactase deficiency in a patient in need thereof, comprising administering an effective amount of a PPARγ agonist compound to said patient, wherein the PPARγ agonist is a compound represented by Formula I':

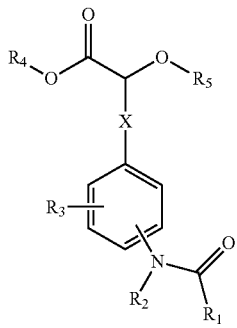

wherein X is $C_1$-$C_3$alkylene, optionally substituted with one, two or three substituents selected from halogen or hydroxyl;

$R_1$ is selected from the group consisting of $C_1$-$C_6$alkyl, $C_3$-$C_6$cycloalkyl, $C_2$-$C_6$alkenyl, and $C_2$-$C_6$alkynyl;

$R_2$ is selected from the group consisting of hydrogen and $C_1$-$C_6$alkyl;

$R_3$ is independently selected, for each occurrence from the group consisting of hydrogen, $C_1$-$C_6$alkoxy, $C_1$-$C_6$alkyl, cyano, $C_3$-$C_6$cycloalkyl, halogen, hydroxyl, and nitro;

$R_4$ is selected from the group consisting of hydrogen and $C_1$-$C_6$alkyl; and $R_5$ is hydrogen $C_1$-$C_6$alkyl;

or a pharmaceutically acceptable salt or an N-oxide thereof.

5. The method of claim 4, wherein the compound is N-acetyl-(R)-3-(4-aminophenyl)-2-methoxypropionic acid or a pharmaceutically acceptable salt thereof.

6. The method of claim 4, wherein the compound is N-acetyl-(S)-3-(4-aminophenyl)-2-methoxypropionic acid or a pharmaceutically acceptable salt thereof.

7. The method of claim 1, wherein the PPARγ agonist is (S)-2-methoxy-3-(4-aminophenyl) propionic acid or a pharmaceutically acceptable salt thereof.

8. The method of claim 1, wherein the PPARγ agonist is 2-methoxy-3-(4-aminophenyl) propionic acid or a pharmaceutically acceptable salt or a stereoisomer thereof.

9. The method of claim 4, wherein the compound is N-acetyl-3-(4-aminophenyl)-2-methoxypropionic acid or a pharmaceutically acceptable salt or a stereoisomer thereof.

* * * * *

SEQUENCE LISTING

```
<160> NUMBER OF SEQ ID NOS: 3

<210> SEQ ID NO 1
<211> LENGTH: 19
<212> TYPE: DNA
<213> ORGANISM: Homo sapiens

<400> SEQUENCE: 1
gcccttcact actgttgac                                                  19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
acgctgagta cttcgaaat                                                  19

<210> SEQ ID NO 3
<211> LENGTH: 3012
<212> TYPE: DNA
<213> ORGANISM: Homo sapiens

<400> SEQUENCE: 3
gtaatttatt ttacttctgt gtcctaaggg taatttctca ggattgtttt caaattgctt     60
ttttagggga aataggtcat ttgctatatt acaagcaatc cccaaatttt atggtcttcc    120
aggaaaagtt attaccgttt atgatactaa cagttcctga gacttagcta tgatcagtat    180
gttcatgagg tggagcagtt cctgtgttgc agcttttaac aacagatggc attcattaaa    240
tcacaaagta tgttaaaggt cacaaaagca aaataactgt ctgaggctaa ggcccacgtg    300
ggacagtcta atacccatga gtactcaact tgccttgatg tctgagcttt ccagtgcaat    360
gtgaatttga gcagccagaa atctattagt agaaagcaag acagattaat ataggttaaa    420
acaatgattt aaatatgttt ctcccaataa ttatctcttt ccctggaatc aacttgtatg    480
aaaccttgtc aaaatgtact ccacaagtat gtacaattaa gtattttaaa aataaatggc    540
aaacattaaa aacaagagtg aatactcaag tagatttgtc atgggatttt tataagaaga    600
ctggtatcag gtaatgtatc tttaaagact aggctgctct gctgacgtag taaccatttt    660
ttattccttt actttcctaa tagccttgct ttcacttaag aaaaaaaaag gctaggcacg    720
gtggctcacg cctgtaatcc cagcactttg ggaggccaag gtgagtagat cacctgaggt    780
caggagttcg agacaagcct ggccaacgtg gagaaaacct gtctctacta aaagtacaaa    840
aattagccag gcatggtggt gggcacctgt aatcccagct actcaggagg ttgaggcagg    900
agaattgctt gaacccaaga ggtggaagtt gcagtgagct gagatcatgc cactgccctc    960
```

```
cagcttgggc ggcaacaaca acaacaaaaa aagattccca ggcttcaccc tctacagtct    1020
atggaaagtc atgggagtct attaaaaaaa aacagacact ataaaccaaa ttaaaagatg    1080
ggaaaatttt tctatcacgt tttaatatgt gatatccaaa ctcccattaa gaatttttat    1140
atcagtaata agataaaact cagaagaaaa atgcccaatt aacaagaaga gcttcacctc    1200
ttaaataatc agaaaagaa aagcacataa tatttacgtc aaagtatcaa aaatgtaaaa    1260
gttttataat aggcattagc aaggcagacg gatacaggca cacatctaac tctatgtagg    1320
atttaacttg gaagacaatt tgcatttcaa tcaatcaaaa accatttttt tttttgagat    1380
gatctccctg tgttgcccag actggcctca agctcctggg cttgagcagt cctacagtct    1440
gagcctccaa aagtactggc aaaacaggcg tgattgacca tgcccagcct gtatataagg    1500
atattcattt gcagcattgt ttgcaacaca aaaatgtaaa accaaccggt gtttaatatg    1560
caagatgtta atttatggta cattcttgct gtggaaagct atgcatctgt tagaggtggg    1620
tctatatgtt ctgatacagg cagaactcta agagctatta agtgaagaaa aggctgaaaa    1680
tacatatggc ataattccat atatgttaaa ttgttctata ttttaaatgt tatacacgtt    1740
tccatttgta tttacgtaat aataatgatc cctgagctgt actgttgtat acatgctaca    1800
agaaagaccc atttaatccc cacagcctat gatgaattat ccacattcta caggtgacaa    1860
aatagaggca caaagttaag taattttttgt caggtgagat ttaaacccag gcattctgac    1920
tcctgtataa ccattaagat atgcagagaa agaaaactgg aaagatacat attgctgaag    1980
atacttatta taggaagagg aggggggagg gtgaaggaat ttgcaagttt ttcatagatg    2040
tttccatatt gtttgaatct cttacaaaat atgttcagca tatttttaaa gagaaaattt    2100
ggggcaaaat acttattttt gtattatgta aacaaatttt aaaataatgt gtggctgggt    2160
gcgctggctc acacctgtaa tcccaacact ttaggaggct gaggcaagag gattgcttga    2220
gcccaggagt tcaagaccag cctgggtgac atggcaaaac tccatctcta ctaaaaatac    2280
aaaaaattag ccagtcgtgg tggcgcacac ctatggtccc acctacccag gatgctgaga    2340
tgggaggatc acttgagccc aggaagtcaa ggctgcagga agctgtgatc gcaccactgc    2400
actcccacct gggcaacaga gtgagacccg gtcaccaaaa aacaaaaaaa acaaaaaaaa    2460
ttggtaatcg ttttcttcag acattttccg ggttcctctg cttaacttgt ataggaagtc    2520
tgaggttttt gtgttggtct ttaccttttt tttttttttt tttttttaag atggagtctc    2580
attctgttgc ccaggctgga gtgcagtggc atgatcttgg ctcctgcaac ctccgcctcc    2640
tgggttcaag tgattctcct gcctcagcct cctgagtagc cgggactaca ggcgcatgcc    2700
acgatgcctg gctaattttt tgtattttta gtagagatgg ggtttcacca tgttagctag    2760
gacggtctcg atctcctgac ctcgtgatcc gcccacctcg gcctcccaaa gtgctggaat    2820
tacaggtgtg agccaccacg cccggccctg atctttacat ttttaaatat tgcattagtg    2880
aaccgtgtac tgattttgtg atcatagata acccagttaa atattaagtc ttaattatca    2940 cttagtatt tacaacctca gttgcagtta taaagtaagg gttccacata cctcctaaca    3000
gttcctagaa aa                                                        3012
```